(12) United States Patent
Gross et al.

(10) Patent No.: US 7,146,209 B2
(45) Date of Patent: Dec. 5, 2006

(54) STIMULATION FOR TREATING EYE PATHOLOGIES

(75) Inventors: Yossi Gross, Moshav Mazor (IL); Alon Shalev, Ra'anana (IL)

(73) Assignee: Brainsgate, Ltd., Ra'anana (IL)

( * ) Notice: Subject to any disclaimer, the term of this patent is extended or adjusted under 35 U.S.C. 154(b) by 498 days.

(21) Appl. No.: 10/294,310

(22) Filed: Nov. 14, 2002

(65) Prior Publication Data

US 2003/0176898 A1    Sep. 18, 2003

Related U.S. Application Data

(63) Continuation-in-part of application No. 10/258,714, filed as application No. PCT/IL01/00402 on May 7, 2001.

(60) Provisional application No. 60/426,180, filed on Nov. 14, 2002, provisional application No. 60/426,181, filed on Nov. 14, 2002, provisional application No. 60/426,182, filed on Nov. 14, 2002, provisional application No. 60/400,167, filed on Jul. 31, 2002, provisional application No. 60/368,657, filed on Mar. 28, 2002, provisional application No. 60/364,451, filed on Mar. 15, 2002, provisional application No. 60/203,172, filed on May 8, 2000.

(51) Int. Cl.
*A61N 1/00* (2006.01)
*A61H 23/00* (2006.01)

(52) U.S. Cl. .......................................................... 607/2
(58) Field of Classification Search ................ 607/1–2, 607/53–54
See application file for complete search history.

(56) References Cited

U.S. PATENT DOCUMENTS 4,152,928 A    5/1979    Roberts
(Continued)

FOREIGN PATENT DOCUMENTS

WO    WO 97/18855    5/1997
(Continued)

OTHER PUBLICATIONS

Delephine, et al., "Plasma Protein Extravasation Induced in the Rat Dura Mater by Stimulation of the Parasympathetic Sphenopalatine Ganglion", Experimental Neurology, 147, 389-400, 1997.
(Continued)

*Primary Examiner*—Robert E. Pezzuto
*Assistant Examiner*—Kristen Mullen
(74) *Attorney, Agent, or Firm*—Abelman, Frayne & Schwab

(57) ABSTRACT

Apparatus is provided for treating a condition of an eye of a subject, comprising a stimulator adapted to stimulate at least one site of the subject, so as to treat the eye condition, the site selected from the list consisting of: a sphenopalatine ganglion (SPG) of the subject, an anterior ethmoidal nerve of the subject, a posterior ethmoidal nerve of the subject, a communicating branch between an anterior ethmoidal nerve and a retro-orbital branch of an SPG of the subject, a communicating branch between a posterior ethmoidal nerve and a retro-orbital branch of an SPG of the subject, a greater palatine nerve of the subject, a lesser palatine nerve of the subject, a sphenopalatine nerve of the subject, a communicating branch between a maxillary nerve and an SPG of the subject, a nasopalatine nerve of the subject, a posterior nasal nerve of the subject, an infraorbital nerve of the subject, an otic ganglion of the subject, an afferent fiber going into the otic ganglion of the subject, an efferent fiber going out of the otic ganglion of the subject, a vidian nerve of the subject, a greater superficial petrosal nerve of the subject, and a lesser deep petrosal nerve of the subject.

49 Claims, 9 Drawing Sheets

U.S. PATENT DOCUMENTS

| | | |
|---|---|---|
| 4,319,580 A | 3/1982 | Colley et al. |
| 4,886,493 A | 12/1989 | Yee |
| 4,979,511 A | 12/1990 | Terry, Jr. et al. |
| 5,031,618 A | 7/1991 | Mullett |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |
| 5,205,285 A | 4/1993 | Baker, Jr. et al. |
| 5,215,086 A | 6/1993 | Terry, Jr. et al. |
| 5,215,089 A | 6/1993 | Baker, Jr. et al. |
| 5,222,494 A | 6/1993 | Baker, Jr. et al. |
| 5,223,254 A | 6/1993 | Paradiso et al. |
| 5,231,988 A | 8/1993 | Wernicke et al. |
| 5,235,980 A | 8/1993 | Varrichio et al. |
| 5,237,991 A | 8/1993 | Baker, Jr. et al. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,304,632 A | 4/1994 | Vaudry et al. |
| 5,330,515 A | 7/1994 | Rutecki et al. |
| 5,335,657 A | 8/1994 | Terry, Jr. et al. |
| 5,351,394 A | 10/1994 | Weinberg |
| 5,531,778 A | 7/1996 | Maschino et al. |
| 5,540,730 A | 7/1996 | Terry, Jr. et al. |
| 5,571,150 A | 11/1996 | Wernicke et al. |
| 5,639,853 A | 6/1997 | Paradiso et al. |
| 5,707,400 A | 1/1998 | Terry, Jr. et al. |
| 5,855,907 A | 1/1999 | Peyman |
| 5,928,272 A | 7/1999 | Adkins et al. |
| 5,938,689 A | 8/1999 | Fischell et al. |
| 5,938,690 A | 8/1999 | Law et al. |
| 6,006,124 A | 12/1999 | Fischell et al. |
| 6,016,449 A | 1/2000 | Fischell et al. |
| 6,061,593 A | 5/2000 | Fischell et al. |
| 6,128,538 A | 10/2000 | Fischell et al. |
| 6,134,474 A | 10/2000 | Fischell et al. |
| 6,161,045 A | 12/2000 | Fischell et al. |
| 6,230,049 B1 | 5/2001 | Fischell et al. |
| 6,232,326 B1 | 5/2001 | Nelson |
| 6,277,841 B1 | 8/2001 | Rajagopalan et al. |
| 6,322,494 B1 | 11/2001 | Bullivant et al. |
| 6,325,475 B1 | 12/2001 | Hayes et al. |
| 6,338,715 B1 | 1/2002 | Hayes et al. |
| 6,353,754 B1 | 3/2002 | Fischell et al. |
| 6,354,299 B1 | 3/2002 | Fischell et al. |
| 6,360,122 B1 | 3/2002 | Fischell et al. |
| 6,405,079 B1 | 6/2002 | Ansarinia |
| 6,410,046 B1 | 6/2002 | Lerner |
| 6,427,086 B1 | 7/2002 | Fischell et al. |
| 6,432,986 B1 | 8/2002 | Levin |
| 6,459,936 B1 | 10/2002 | Fischell et al. |
| 6,466,822 B1 | 10/2002 | Pless |
| 6,473,639 B1 | 10/2002 | Fischell et al. |
| 6,473,644 B1 | 10/2002 | Terry, Jr. et al. |
| 6,480,743 B1 | 11/2002 | Kirkpatrick et al. |
| 6,491,940 B1 | 12/2002 | Levin |
| 6,526,318 B1 | 2/2003 | Ansarinia |
| 6,529,774 B1 | 3/2003 | Greene |
| 6,531,454 B1 | 3/2003 | Leary et al. |
| 6,587,719 B1 | 7/2003 | Barrett et al. |
| 6,591,137 B1 | 7/2003 | Fischell et al. |
| 6,591,138 B1 | 7/2003 | Fischell et al. |
| 6,597,953 B1 | 7/2003 | Boling |
| 6,597,954 B1 | 7/2003 | Pless et al. |
| 6,606,521 B1 | 8/2003 | Paspa et al. |
| 6,609,025 B1 | 8/2003 | Barrett et al. |
| 6,609,956 B1 | 8/2003 | Margaria |
| 6,618,623 B1 | 9/2003 | Pless et al. |
| 6,622,038 B1 | 9/2003 | Barrett et al. |
| 6,622,041 B1 | 9/2003 | Terry et al. |
| 6,622,047 B1 | 9/2003 | Barrett et al. |
| 6,647,296 B1 | 11/2003 | Fischell et al. |
| 6,662,035 B1 | 12/2003 | Sochor |
| 6,678,553 B1 | 1/2004 | Lerner et al. |
| 6,690,974 B1 | 2/2004 | Archer et al. |
| 6,735,475 B1 | 5/2004 | Whitehurst |
| 6,788,975 B1 | 9/2004 | Whitehurst |
| 6,810,285 B1 | 10/2004 | Pless et al. |
| 6,811,788 B1 | 11/2004 | Yu |
| 6,853,858 B1 | 2/2005 | Shalev |
| 6,905,827 B1 | 6/2005 | Wohlgemuth et al. |
| 2001/0004644 A1 | 6/2001 | Levin |
| 2002/0026652 A1 | 2/2002 | Allen et al. |
| 2002/0044919 A1 | 4/2002 | Yu |
| 2002/0068080 A1 | 6/2002 | Lerner |
| 2002/0082583 A1 | 6/2002 | Lerner |
| 2002/0099412 A1 | 7/2002 | Fischell et al. |
| 2002/0123678 A1 | 9/2002 | Lerner et al. |
| 2002/0133841 A1 | 9/2002 | Leviten |
| 2002/0169307 A1 | 11/2002 | Klein |
| 2002/0169485 A1 | 11/2002 | Pless et al. |
| 2002/0183683 A1 | 12/2002 | Lerner |
| 2003/0005473 A1 | 1/2003 | Brennan et al. |
| 2003/0005477 A1 | 1/2003 | Leviten |
| 2003/0013136 A1 | 1/2003 | Balser et al. |
| 2003/0014772 A1 | 1/2003 | Allen |
| 2003/0018988 A1 | 1/2003 | Allen et al. |
| 2003/0018989 A1 | 1/2003 | Wisotzkey et al. |
| 2003/0051268 A1 | 3/2003 | Sasselli |
| 2003/0056238 A1 | 3/2003 | Albiston et al. |
| 2003/0073917 A1 | 4/2003 | Echauz et al. |
| 2003/0074033 A1 | 4/2003 | Pless et al. |
| 2003/0106083 A1 | 6/2003 | Nelson |
| 2003/0131367 A1 | 7/2003 | Vaudry et al. |
| 2003/0133877 A1 | 7/2003 | Levin |
| 2003/0144711 A1 | 7/2003 | Pless et al. |
| 2003/0149457 A1 | 8/2003 | Tcheng et al. |
| 2003/0166099 A1 | 9/2003 | Sabbadini et al. |
| 2003/0166279 A1 | 9/2003 | Sabbadini et al. |
| 2003/0172390 A1 | 9/2003 | Wisotzkey et al. |
| 2003/0176892 A1 | 9/2003 | Shalev |
| 2003/0176898 A1 | 9/2003 | Griss et al. |
| 2003/0177514 A1 | 9/2003 | Sasselli |
| 2003/0190601 A1 | 10/2003 | Sabbadini et al. |
| 2003/0190683 A1 | 10/2003 | Sabbadini et al. |
| 2003/0190749 A1 | 10/2003 | Surber et al. |
| 2003/0191426 A1 | 10/2003 | Lerner et al. |
| 2003/0194714 A1 | 10/2003 | Sabbadini et al. |
| 2003/0195588 A1 | 10/2003 | Fischell et al. |
| 2003/0195602 A1 | 10/2003 | Boling |
| 2003/0198995 A1 | 10/2003 | Sabbadini et al. |
| 2003/0198996 A1 | 10/2003 | Surber et al. |
| 2003/0199005 A1 | 10/2003 | Sabbadini et al. |
| 2003/0199088 A1 | 10/2003 | Sabbadini et al. |
| 2003/0199089 A1 | 10/2003 | Surber et al. |
| 2003/0202937 A1 | 10/2003 | Sabbadini et al. |
| 2003/0203411 A1 | 10/2003 | Sabbadini et al. |
| 2003/0203481 A1 | 10/2003 | Surber et al. |
| 2003/0207833 A1 | 11/2003 | Berkley et al. |
| 2003/0211086 A1 | 11/2003 | Berkley et al. |
| 2003/0211599 A1 | 11/2003 | Sabbadini et al. |
| 2003/0219408 A1 | 11/2003 | Sabbadini et al. |
| 2003/0219888 A1 | 11/2003 | Segall et al. |
| 2003/0224369 A1 | 12/2003 | Surber et al. |
| 2003/0224444 A1 | 12/2003 | Sabbadini et al. |
| 2003/0232335 A1 | 12/2003 | Surber et al. |
| 2004/0015068 A1 | 1/2004 | Shalev et al. |
| 2004/0033491 A1 | 2/2004 | Alsobrook et al. |
| 2004/0054297 A1 | 3/2004 | Wingeier et al. |
| 2004/0136950 A1 | 7/2004 | Ni et al. |
| 2004/0136951 A1 | 7/2004 | Ni et al. |

| | | | |
|---|---|---|---|
| 2004/0153129 | A1 | 8/2004 | Pless et al. |
| 2004/0210269 | A1 | 10/2004 | Shalev et al. |
| 2004/0220644 | A1 | 11/2004 | Shalev et al. |
| 2005/0020519 | A1 | 1/2005 | Albiston et al. |
| 2005/0054939 | A1 | 3/2005 | Ben-Ari et al. |
| 2005/0074506 | A1 | 4/2005 | Natan et al. |
| 2005/0112090 | A9 | 5/2005 | Ni et al. |
| 2005/0118187 | A1 | 6/2005 | Yu |
| 2005/0137646 | A1 | 6/2005 | Wallace et al. |
| 2005/0137647 | A1 | 6/2005 | Wallace et al. |
| 2005/0159790 | A1 | 7/2005 | Shalev |
| 2006/0155344 | A1* | 7/2006 | Rezai et al. .......... 607/46 |

FOREIGN PATENT DOCUMENTS

| | | |
|---|---|---|
| WO | WO 99/03473 | 1/1999 |
| WO | WO 00/44432 | 8/2000 |
| WO | WO 01/43733 | 6/2001 |
| WO | WO 01/85094 | 11/2001 |
| WO | WO 03/063959 | 8/2003 |
| WO | WO 03/076008 | 9/2003 |
| WO | WO 03/090599 | 11/2003 |
| WO | WO 03/105658 | 12/2003 |
| WO | WO 04/010923 | 2/2004 |
| WO | WO 04/043217 | 5/2004 |
| WO | WO 04/043218 | 5/2004 |
| WO | WO 04/043334 | 5/2004 |
| WO | WO 04/044947 | 5/2004 |
| WO | WO 04/045242 | 5/2004 |
| WO | WO 02/002467 | 1/2005 |
| WO | WO 05/030025 | 4/2005 |
| WO | WO 05/030118 | 4/2005 |

OTHER PUBLICATIONS

Hara H. Zhang, et al., "Parasympathetic Cerebrovascular Innervation: An Anterograde Tracing from the Sphenopalatine Ganglion in the Rat", Neurosurgery, 32, 822-827, 1993.

G.L. Ruskell, "The Orbital Branches of the Pterygopalatine Ganglion and their Relationship with Internal Carotid Nerve Branches in Primates", J. Anat. 1970, 106, 2, pp. 323-339.

Kroll RA, Neuwelt EA, "Outwitting the Blood Brain Barrier for Therapeutic Purposes: Osmotic Opening and Other Means", Neurosurgery, 42, 1083-1100, 1998.

Sanders M, et al., "Efficacy of Sphenopalatine Ganglion Blockade in 66 Patients Suffering from Cluster Headache: A 12-70 Month Follow-Up Evaluation", Journal of Neurosurgery, 87, 876-880, 1997.

Gloria Lee, et al, "Drug Transporters in the Central Nervous System: Brain Barriers and Brain Perenchyma Considerations", Pharmacol Rev vol. 53, No. 4, pp. 569-596, 2001.

Van de WaterBeemd, et al., "Estimation of Blood Brain Barrier Crossing of Drugs Using Molecular Size and Shape and H bonding Descriptors", Journal of Drug Targeting, 6, 151-165, 1998.

Suzuki, N. et al., "Selective Electrical Stimulation of postganglionic Cerebrovascular Parasympathetic Nerve Fibers Originating from the Sphenopalatine Ganglion Enhances Cortical Blood Flow in the Rat", Journal of Cerebral Blood Flow and Metabolism, 10, 383-391 (1990).

Suzuki, N. et al., "Effect on Cortical Blood Flow of Electrical Stimulation of Trigeminal Cerebrovascular Nerve Fibers in the Rat", Acta Physiol. Scand., 138, 307-315, 1990.

Samad TA et al., in an article entitled, "Interleukin-1beta-mediated induction of Cox-2 in the CNS contributes to inflammatory pain hypersensitivity," in Nature 410(6827):471-5 (2001).

Major A, Silver W, "Odorants presented to the rat nasal cavity increase cortical blood flow," Chem. Senses, 24, 665-669 (1999).

Fusco BM, Fiore G, Gallo F, Martelletti P, Giacovazzo M, "'Capsaicin-sensitive' sensory neurons in cluster headache: pathophysiological aspects and therapeutic indications," Headache, 34, 132-137 (1994).

Lambert GA, Bogduk N, Goadsby PJ, Duckworth JW, Lance JW, "Decreased carotid arterial resistance in cats in response to trigeminal stimulation," Journal of Neurosurgery, 61, 307-315 (1984).

Silver WL, "Neural and pharmacological basis for nasal irritation," in Tucker WG, Leaderer BP, Molhave L, Cain WS (eds), Sources of Indoor Air Contaminants, Ann. NY Acad. Sci., 641, 152-163 (1992).

Branston NM, "The physiology of the cerebrovascular parasympathetic innervation," British Journal of Neurosurgery 9:319-329 (1995).

Branston NM et al., "Contribution of cerebrovascular parasympathetic and sensory innervation to the short-term control of blood flow in rat cerebral cortex," J Cereb Blood Flow Metab 15(3):525-31 (1995).

Toda N et al., "Cerebral vasodilation induced by stimulation of the pterygopalatine ganglion and greater petrosal nerve in anesthetized monkeys," Neuroscience 96(2):393-398 (2000).

Seylaz J et al., "Effect of stimulation of the sphenopalatine ganglion on cortical blood flow in the rat," J Cereb Blood Flow Metab 8(6):875-8 (1988).

Rucci L et al., "Histamine release from nasal mucosal mast cells in patients with chronic hypertrophic non-allergic rhinitis, after parasympathetic nerve stimulation," Agents Actions 25(3-4):314-20 (1988).

L. Rucci, et al, "Effects of Vidian Nerve Stimulation on the Nasal and Maxillary Sinus Mucosa", The Journal of Laryngology and Otology, Jun. 1984, vol. 98, pp. 597-607.

N. Toda, et al, "Preganglionic and Postganglionic Neurons Responsible for Cerebral Vasodilation Mediated by Nitric Oxide in Anesthetized Dogs", J Cereb Blood Flow Metab. vol. 20 No. 4, 2000.

Ronald F. Young, "Electrical Stimulation of the Trigeminal nerve root for the Treatment of Chronic Facial Pain", J Neurosurg 83:72-78, 1995.

L. Rucci, et al, "Vidian Nerve Resection in Chronic Hypertrophic Non Allergic Rhinitis: Effects on Histamine Content, Number and Rate of Degranulation Processes of Mast Cells in Nasal Mucosa", Rhinology, 23, 309-314, 1985.

L. Rucci, et al., "Tympanometric Variations Induced by Vidian Nerve Stimulation in Humans", The Journal of Laryngology and Otology, Apr. 1985, vol. 99, pp. 355-358.

E. Masini, et al., "Stimulation ans Resection of Vidian Nerve in Patients with Chronic Non-Allergic Rhinitis: Effect on Histamine Content in Nasal Mucosa", Agents and Actions, vol. 18, ½ 1986.

H. Bolay, et al, "Intrinsic Brain Activity Triggers Trigeminal Meningeal Afferents in a Migraine Model", Feb. 2002, vol. 8 No. 2, pp. 136-142.

N. Suzuki, et al, "Origins and Pathways of Cerebrovascular Vasoactive Intestinal Polypeptide-Positive Nerves in Rat", J Cereb Blood Flow Metab. vol. 8 No. 5, 1988.

U.S. Appl. No. 60/265,008.

Office Action dated Mar. 16, 2006 in U.S. Appl. No. 10/258,714, filed Jan. 22, 2003.

Office Action dated Dec. 16, 2005 in U.S. Appl. No. 10/753,882, filed Jan. 9, 2004.

Office Action dated Mar. 16, 2006 in U.S. Appl. No. 10/753,882 (second action in same case as above), filed Jan. 9, 2004.

* cited by examiner

STIMULATION FOR TREATING EYE PATHOLOGIES

CROSS-REFERENCES TO RELATED APPLICATIONS

This application is a continuation-in-part of U.S. patent application Ser. No. 10/258,714 to Shalev and Gross, filed Jan. 22, 2003, entitled, "Method and apparatus for stimulating the sphenopalatine ganglion to modify properties of the BBB and cerebral blood flow," which is a US national phase application corresponding to PCT Patent Application PCT/IL01/00402, filed May 7, 2001, entitled, "Method and apparatus for stimulating the sphenopalatine ganglion to modify properties of the BBB and cerebral blood flow," which claims priority from U.S. Provisional Patent Application 60/203,172, filed May 8, 2000, entitled, "Method and apparatus for stimulating the sphenopalatine ganglion to modify properties of the BBB and cerebral blood flow."

This application claims priority from: (i) U.S. Provisional Patent Application 60/400,167, filed Jul. 31, 2002, entitled, "Delivering compounds to the brain by modifying properties of the BBB and cerebral circulation," and (ii) U.S. Provisional Patent Application 60/364,451, filed Mar. 15, 2002, entitled, "Applications of stimulating the sphenopalatine ganglion (SPG)." This application also claims priority from (iii) U.S. Provisional Application No. 60/368,657 filed Mar. 28, 2002 entitled, "SPG Stimulation".

This application is related to: (i) U.S. provisional patent application 60/426,180 to Lorian et al., filed Nov. 14, 2002, entitled, "Surgical tools and techniques for stimulation," (ii) U.S. provisional patent application 60/426,182 to Gross et al., filed Nov. 14, 2002, entitled, "Stimulation circuitry and control of electronic medical device," and (iii) U.S. provisional patent application 60/426,181 to Shalev et al., filed Nov. 14, 2002, entitled, "Stimulation for treating ear pathologies."

Each of the above-cited patent applications is assigned to the assignee of the present patent application and is incorporated herein by reference.

FIELD OF THE INVENTION

The present invention relates generally to medical procedures and electrical devices. More specifically, the invention relates to the use of electrical, chemical, mechanical and/or odorant stimulation for treating eye pathologies.

BACKGROUND OF THE INVENTION

The blood-brain barrier (BBB) is a unique feature of the central nervous system (CNS) which isolates the brain from the systemic blood circulation. To maintain the homeostasis of the CNS, the BBB prevents access to the brain of many substances circulating in the blood.

The BBB is formed by a complex cellular system of endothelial cells, astroglia, pericytes, perivascular macrophages, and a basal lamina. Compared to other tissues, brain endothelia have the most intimate cell-to-cell connections: endothelial cells adhere strongly to each other, forming structures specific to the CNS called "tight junctions" or zonula occludens. They involve two opposing plasma membranes which form a membrane fusion with cytoplasmic densities on either side. These tight junctions prevent cell migration or cell movement between endothelial cells. A continuous uniform basement membrane surrounds the brain capillaries. This basal lamina encloses contractile cells called pericytes, which form an intermittent layer and probably play some role in phagocytosis activity and defense if the BBB is breached. Astrocytic end feet, which cover the brain capillaries, build a continuous sleeve and maintain the integrity of the EBB by the synthesis and secretion of soluble growth factors (e.g., gamma-glutamyl transpeptidase) essential for the endothelial cells to develop their BBB characteristics.

PCT Patent Publication WO 01/85094 to Shalev and Gross, which is assigned to the assignee of the present patent application and is incorporated herein by reference, describes apparatus for modifying a property of a brain of a patient, including electrodes applied to a sphenopalatine ganglion (SPG) or a neural tract originating in or leading to the SPG. A control unit drives the electrodes to apply a current capable of inducing (a) an increase in permeability of a blood-brain barrier (BBB) of the patient, (b) a change in cerebral blood flow of the patient, and/or (c) an inhibition of parasympathetic activity of the SPG.

U.S. Pat. No. 5,756,071 to Mattern et al., which is incorporated herein by reference, describes a method for nasally administering aerosols of therapeutic agents to enhance penetration of the blood brain barrier. The patent describes a metering spray designed for pernasal application, the spray containing at least one sex hormone or at least one metabolic precursor of a sex hormone or at least one derivative of a sex hormone or combinations of these, excepting the precursors of testosterone, or at least one biogenic amine, with the exception of catecholamines.

U.S. Pat. No. 5,752,515 to Jolesz et al., which is incorporated herein by reference, describes apparatus for image-guided ultrasound delivery of compounds through the blood-brain barrier. Ultrasound is applied to a site in the brain to effect in the tissues and/or fluids at that location a change detectable by imaging. At least a portion of the brain in the vicinity of the selected location is imaged, e.g., via magnetic resonance imaging, to confirm the location of that change. A compound, e.g., a neuropharmaceutical, in the patient's bloodstream is delivered to the confirmed location by applying ultrasound to effect opening of the blood-brain barrier at that location and, thereby, to induce uptake of the compound there.

PCT Publication WO 01/97905 to Ansarinia, which is incorporated herein by reference, describes a method for the suppression or prevention of various medical conditions, including pain, movement disorders, autonomic disorders, and neuropsychiatric disorders. The method includes positioning an electrode on or proximate to at least one of the patient's SPG, sphenopalatine nerves, or vidian nerves, and activating the electrode to apply an electrical signal to such nerve. In a further embodiment for treating the same conditions, the electrode used is activated to dispense a medication solution or analgesic to such nerve. The '905 publication also describes surgical techniques for implanting the electrode.

U.S. Pat. No. 6,405,079 to Ansarinia, which is incorporated herein by reference, describes a method for the suppression or prevention of various medical conditions, including pain, movement disorders, autonomic disorders, and neuropsychiatric disorders. The method includes positioning an electrode adjacent to or around a sinus, the dura adjacent a sinus, or falx cerebri, and activating the electrode to apply an electrical signal to the site. In a further embodiment for treating the same conditions, the electrode dispenses a medication solution or analgesic to the site. The '079 patent also describes surgical techniques for implanting the electrode.

U.S. Pat. No. 6,294,544 to Araie et al., which is incorporated herein by reference, describes a peripheral ocular circulation ameliorant which contains dihydropyridines, for treating visual field defects associated with normal intraocular pressure glaucoma as well as for optic neuropathy, retinopathy, and retinal-degeneration diseases.

U.S. Pat. No. 5,431,907 to Abelson et al., which is incorporated herein by reference, describes the administration of calcium channel blocking agents to the eye to treat ischemic disorders of the retina and associated tissues of the posterior segment of the eye, by increasing blood flow to these tissues.

U.S. Pat. No. 6,451,799 to Ogawa et al., which is incorporated herein by reference, describes an ocular circulation ameliorant which contains a 1,4-dihydropyridine derivative, for treating glaucoma, particularly normal tension glaucoma caused by ocular circulation disorder and retinitis pigmentosa, macular degeneration, ischemic optic neuropathy, iridocyclitis, retinal artery occlusion, retinal vein occlusion, diabetic retinopathy, ischemic optic neuropathy, retinochoroidal disease following choroidal lesion, and retinochoroidal disease associated with systemic disease.

The following references, which are incorporated herein by reference, may be useful:

Delepine L, Aubineau P, "Plasma protein extravasation induced in the rat dura mater by stimulation of the parasympathetic sphenopalatine ganglion," Experimental Neurology, 147, 389–400 (1997)

Hara H, Zhang Q J, Kuroyanagi T, Kobayashi S, "Parasympathetic cerebrovascular innervation: An anterograde tracing from the sphenopalatine ganglion in the rat," Neurosurgery, 32, 822–827 (1993)

Jolliet-Riant P, Tillement J P, "Drug transfer across the blood-brain barrier and improvement of brain delivery," Fundam. Clin. Pharmacol., 13, 16–25 (1999)

Kroll R A, Neuwelt E A, "Outwitting the blood brain barrier for therapeutic purposes: Osmotic opening and other means," Neurosurgery, 42, 1083–1100 (1998)

Sanders M, Zuurmond W W, "Efficacy of sphenopalatine ganglion blockade in 66 patients suffering from cluster headache: A 12–70 month follow-up evaluation," Journal of Neurosurgery, 87, 876–880 (1997)

Syelaz J, Hara H, Pinard E, Mraovitch S, MacKenzie E T, Edvinsson L, "Effects of stimulation of the sphenopalatine ganglion on cortical blood flow in the rat," Journal of Cerebral Blood Flow and Metabolism," 8, 875–878 (1988)

Van de Waterbeemd H, Camenisch G, Folkers G, Chretien J R, Raevsky O A, "Estimation of blood brain barrier crossing of drugs using molecular size and shape and h bonding descriptors," Journal of Drug Targeting," 6, 151–165, (1998)

Suzuki N, Hardebo J E, Kahrstrom J, Owman C, "Selective electrical stimulation of postganglionic cerebrovascular parasympathetic nerve fibers originating from the sphenopalatine ganglion enhances cortical blood flow in the rat," Journal of Cerebral Blood Flow and Metabolism, 10, 383–391 (1990)

Suzuki N, Hardebo J E, Kahrstrom J, Owman C H, "Effect on cortical blood flow of electrical stimulation of trigeminal cerebrovascular nerve fibres in the rat," Acta Physiol. Scand., 138, 307–315 (1990)

Major A, Silver W, "Odorants presented to the rat nasal cavity increase cortical blood flow," Chem. Senses, 24, 665–669 (1999)

Fusco B M, Fiore G, Gallo F, Martelletti P, Giacovazzo M, "'Capsaicin-sensitive' sensory neurons in cluster headache: pathophysiological aspects and therapeutic indications," Headache, 34, 132–137 (1994)

Lambert G A, Bogduk N, Goadsby P J, Duckworth J W, Lance J W, "Decreased carotid arterial resistance in cats in response to trigeminal stimulation," Journal of Neurosurgery, 61, 307–315 (1984)

Silver W L, "Neural and pharmacological basis for nasal irritation," in Tucker W G, Leaderer B P, Mølhave L, Cain W S (eds), Sources of Indoor Air Contaminants, Ann. NY Acad. Sci., 641, 152–163 (1992)

Silver W, "Chemesthesis: the burning questions," ChemoSense, Vol. 2, 1–2 (1999)

Devoghel J C, "Cluster headache and sphenopalatine block," Acta Anaesthesiol Belg., 32 (1):101–7 (1981)

SUMMARY OF THE INVENTION

It is an object of some aspects of the present invention to provide improved methods and apparatus for treating conditions of the eye. Unless usage indicates otherwise, in the context of the present patent application and in the claims, the word "eye" is meant to include the eyeball, vitreous body, choroid, optic nerve, pupil, lens, ciliary body, macula, retina, sclera, iris, cornea, conjunctiva, and the vasculature carrying blood to/from the eye.

It is an additional object of some aspects of the present invention to provide improved methods and apparatus for delivery of compounds to the eye.

It is yet an additional object of some aspects of the present invention to provide improved methods and apparatus for delivery of compounds to the eye through the blood brain barrier (BBB).

It is still an additional object of some aspects of the present invention to provide improved methods and apparatus for treating eye conditions by increasing blood flow to the eye.

It is also an additional object of some aspects of the present invention to provide improved methods and apparatus for treating eye conditions by increasing the clearance of fluid and/or molecules (e.g., metabolites) from the eye.

It is also an object of some aspects of the present invention to provide such methods and apparatus as can be employed to deliver such compounds through the BBB to the eye using a minimally invasive approach.

It is a further object of some aspects of the present invention to provide such methods and apparatus as can facilitate delivery of large molecular weight compounds through the BBB to the eye, such as, for example, (a) pharmaceutical products having high intrinsic molecular weight, or (b) pharmaceutical products (e.g., NSAIDs) having low molecular weight, but are extensively bound to high molecular weight compounds (e.g., albumin). In the context of the present patent application, descriptions of facilitating the movement of "large" or "high molecular weight" molecules includes compounds drawn from both (a) and (b).

It is yet a further object of some aspects of the present invention to provide cost-effective methods and apparatus for delivery of compounds through the BBB to the eye.

It is still a further object of some aspects of the present invention to provide improved methods and apparatus for treating tumors of the optic nerve and other structures of the eye via delivery of compounds through the BBB.

It is also an object of some aspects of the present invention to provide implantable apparatus which affects a property of the eye, without actually being implanted in the eye.

It is a further object of some aspects of the present invention to provide methods which affect a property of the eye without the use of implantable apparatus.

It is yet a further object of some aspects of the present invention to affect a property of the eye by using the neuroexcitatory and/or neuroinhibitory effects of odorants on nerves in the head.

These and other objects of the invention will become more apparent from the description of preferred embodiments thereof provided hereinbelow.

In some preferred embodiments of the present invention, conditions of the eye are treated by stimulating at least one "modulation target site" (MTS), as defined hereinbelow, by applying electrical, chemical, mechanical and/or odorant stimulation to the site. For some conditions, such as some ocular vascular disorders, such stimulation is configured so as to increase cerebral blood flow (CBF), thereby increasing blood flow to various tissues of the eye and treating the condition. Alternatively or additionally, such stimulation is configured to increase permeability of the BBB, in order to enhance delivery of therapeutic molecules from the systemic blood circulation across the BBB and into the eye, so as to treat tumors and other conditions of the eye. The electrical, chemical, mechanical and odorant stimulation techniques described herein may treat a number of eye conditions, including, but not limited to, diabetic retinopathies, retinal vein occlusion, retinal artery occlusion, retinal detachment, tumors of the eye (including tumors of the optic nerve), macular degeneration, glaucoma, and cystoid macular edema (CME).

In the present patent application, including the claims, a "modulation target site" (MTS) consists of:
- a sphenopalatine ganglion (SPG) (also called a pterygopalatine ganglion);
- an anterior ethmoidal nerve;
- a posterior ethmoidal nerve;
- a communicating branch between the anterior ethmoidal nerve and the SPG (retro-orbital branch);
- a communicating branch between the posterior ethmoidal nerve and the SPG (retro-orbital branch)
- a nerve of the pterygoid canal (also called a vidian nerve), such as a greater superficial petrosal nerve (a preganglionic parasympathetic nerve) or a lesser deep petrosal nerve (a postganglionic sympathetic nerve);
- a greater palatine nerve;
- a lesser palatine nerve;
- a sphenopalatine nerve;
- a communicating branch between the maxillary nerve and the sphenopalatine ganglion;
- a nasopalatine nerve;
- a posterior nasal nerve;
- an infraorbital nerve;
- an otic ganglion;
- an afferent fiber going into the otic ganglion; and/or
- an efferent fiber going out of the otic ganglion.

In some preferred embodiments of the present invention, the electrical, chemical, mechanical and/or odorant stimulation techniques described herein enhance delivery of therapeutic molecules across the BBB by modulation of at least one MTS and/or another parasympathetic center. These techniques typically stimulate the nerve fibers of the MTS, thereby inducing the middle and anterior cerebral arteries to dilate, and also causing the walls of these cerebral arteries to become more permeable to large molecules. In this manner, the movement of large pharmaceutical molecules from within blood vessels to the cerebral tissue, and from the cerebral tissue to tissue of the eye, is substantially increased.

In particular, these embodiments may be adapted for delivering chemotherapy agents, which typically comprise large molecules to structures of the eye. Without the use of the techniques described herein, the intact BBB generally blocks the passage of these compounds to the eye.

It is to be appreciated that references herein to specific modulation target sites are to be understood as including other modulation target sites, as appropriate.

It is further to be appreciated that implantation and modulation sites, methods of implantation, and parameters of modulation are described herein by way of illustration and not limitation, and that the scope of the present invention includes other possibilities which would be obvious to someone of ordinary skill in the art who has read the present patent application.

It is yet further to be appreciated that while some preferred embodiments of the invention are generally described herein with respect to electrical transmission of power and electrical modulation of tissue, other modes of energy transport may be used as well. Such energy includes, but is not limited to, direct or induced electromagnetic energy, radiofrequency (RF) transmission, mechanical vibration, ultrasonic transmission, optical power, and low power laser energy (via, for example, a fiber optic cable).

It is additionally to be appreciated that whereas some preferred embodiments of the present invention are described with respect to application of electrical currents to tissue, this is to be understood in the context of the present patent application and in the claims as being substantially equivalent to applying an electrical field, e.g., by creating a voltage drop between two electrodes.

In some preferred embodiments of the present invention, stimulation of at least one MTS is achieved by presenting odorants to an air passage of a patient, such as a nasal cavity or the throat, so as to treat an eye condition. The temporal profile and other quantitative characteristics of such odorant modulation are believed by the present inventors to have a mechanism of action that has a neuroanatomical basis overlapping with that of the electrical modulation of the SPG or another MTS. Furthermore, experimental animal evidence collected by the inventors and described in U.S. Provisional Patent Application 60/368,657 to Shalev and Gross entitled, "SPG stimulation," filed Mar. 28, 2002, which is assigned to the assignee of the present invention and is incorporated herein by reference, suggest a correlation between the mechanisms of increasing cerebral blood flow and increased cerebrovascular permeability. For some applications, odorant-presentation techniques for treating an eye condition described herein are practiced in combination with techniques described in U.S. Provisional Patent Application 60/376,048, filed Apr. 25, 2002, entitled, "Methods and apparatus for modifying properties of the BBB and cerebral circulation by using the neuroexcitatory and/or neuroinhibitory effects of odorants on nerves in the head," which is assigned to the assignee of the present patent application and is incorporated herein by reference.

Odorants that may increase or decrease cerebral blood flow and/or the permeability of the BBB, and which are suitable for treating an eye condition, include, but are not limited to, propionic acid, cyclohexanone, amyl acetate, acetic acid, citric acid, carbon dioxide, sodium chloride, ammonia, menthol, alcohol, nicotine, piperine, gingerol, zingerone, allyl isothiocyanate, cinnamaldehyde, cuminaldehyde, 2-propenyl/2-phenylethyl isothiocyanate, thymol, and eucalyptol.

The odorants reach the appropriate neural structures and induce vasodilatation, vasoconstriction and/or cerebrovascular permeability changes. Delivery of a drug to the eye via the brain can be achieved by mixing the drug with the odorant; by intravenously, intraperitoneally, or intramuscularly administering the drug while the odorant is having an effect, or therebefore; or by other delivery methods known in the art.

In some preferred embodiments of the present invention, stimulation of at least one MTS is achieved by applying a neuroexcitatory agent to the MTS. Suitable neuroexcitatory agents include, but are not limited to acetylcholine and urocholine. For some applications, the MTS is stimulated by applying a neuroinhibitory agent, such as atropine, hexamethonium, or a local anesthetic (e.g., lidocaine).

In some preferred embodiments of the present invention, stimulation of the MTS is achieved by applying mechanical stimulation to the MTS, e.g., vibration.

As described above, it is believed that substantially all pharmacological treatments aimed at structures of the eye are amenable for use in combination with techniques described herein, including electrical, odorant, chemical and mechanical techniques for stimulating at least one MTS. In particular, these embodiments of the present invention may be adapted for use in facilitating the administration of chemotherapeutic drugs.

There is therefore provided, in accordance with an embodiment of the present invention, apparatus for treating a condition of an eye of a subject, including a stimulator adapted to stimulate at least one site of the subject, so as to treat the eye condition, the site selected from the list consisting of: a sphenopalatine ganglion (SPG) of the subject, an anterior ethmoidal nerve of the subject, a posterior ethmoidal nerve of the subject, a communicating branch between an anterior ethmoidal nerve and a retro-orbital branch of an SPG of the subject, a communicating branch between a posterior ethmoidal nerve and a retro-orbital branch of an SPG of the subject, a greater palatine nerve of the subject, a lesser palatine nerve of the subject, a sphenopalatine nerve of the subject, a communicating branch between a maxillary nerve and an SPG of the subject, a nasopalatine nerve of the subject, a posterior nasal nerve of the subject, an infraorbital nerve of the subject, an otic ganglion of the subject, an afferent fiber going into the otic ganglion of the subject, an efferent fiber going out of the otic ganglion of the subject, a vidian nerve of the subject, a greater superficial petrosal nerve of the subject, and a lesser deep petrosal nerve of the subject.

In an embodiment, the apparatus is adapted to treat one or more of the following eye conditions:
diabetic retinopathy;
retinal vein occlusion;
retinal artery occlusion;
retinal detachment;
macular degeneration;
glaucoma;
an optic neuropathy;
retinal degeneration;
cystoid macular edema (CME);
a tumor of the eye;
a tumor of an optic nerve of the subject; and/or
retinal carcinoma.

In an embodiment, the stimulator is adapted to configure the stimulation of the site to cause an increase in cerebral blood flow (CBF) of the subject, so as to treat the eye condition.

In an embodiment, the stimulator is adapted to configure the stimulation of the site to cause an increase in molecular passage across a blood brain barrier (BBB) of the subject.

In an embodiment, the stimulator is adapted to configure the stimulation of the site to increase molecular passage across the BBB to a magnitude that increases passage of a therapeutic agent from a systemic blood circulation of the patient through the BBB into a vicinity of the eye of the subject, so as to treat the eye condition.

In an embodiment, the stimulator includes an electrical stimulator, adapted to drive a current into the site, so as to stimulate the site. In an embodiment, the electrical stimulator is adapted to be implanted in a body of the subject. In an embodiment, the electrical stimulator is adapted to be implanted at an implantation site in or adjacent to an orbital cavity of the subject.

In an embodiment, the electrical stimulator includes at least one electrode, adapted to be placed in a vicinity of an ethmoidal nerve of the subject. In an embodiment, the electrode is adapted to be implanted in the vicinity of the ethmoidal nerve. In an embodiment, the electrode is adapted to be placed in a vicinity of an anterior ethmoidal nerve of the subject. Alternatively, the electrode is adapted to be placed in a vicinity of a posterior ethmoidal nerve of the subject.

In an embodiment, the electrical stimulator includes:
at least one electrode, adapted to be placed in a vicinity of the site; and
a control unit, adapted to drive the electrode to apply the current to the site.

The electrode may be adapted to be implanted in the vicinity of the site.

In an embodiment, the site includes a first site and a second site, different from the first site, and the at least one electrode includes a first electrode and a second electrode, the first electrode adapted to be placed in a vicinity of the first site, and the second electrode adapted to be placed in a vicinity of the second site.

In an embodiment, the first site includes the vidian nerve of the subject, and the second site includes an SPG of the subject, and the first electrode is adapted to be placed in a vicinity of the vidian nerve, and the second electrode is adapted to be placed in a vicinity of the SPG.

In an embodiment, the stimulator includes a chemical stimulator device, adapted to apply a neuroexcitatory agent to the site, so as to stimulate the site. In an embodiment, the neuroexcitatory agent includes acetylcholine, and the chemical stimulator device is adapted to apply the acetylcholine. Alternatively or additionally, the neuroexcitatory agent includes urocholine, and the chemical stimulator device is adapted to apply the urocholine.

In an embodiment, the stimulator includes a mechanical stimulator device, adapted to apply mechanical stimulation to the site. In an embodiment, the mechanical stimulator device is adapted to apply vibration to the site. In an embodiment, the stimulator is adapted to configure the stimulation of the site to cause an increase in a blood flow of the eye, so as to treat the eye condition. In an embodiment, the stimulator is adapted to configure the stimulation of the site to cause the increased blood flow of the eye to be of a magnitude that increases clearance of a substance from at least a portion of the eye, so as to treat the eye condition. In an embodiment, the substance includes a fluid contained in an anterior chamber of the eye, and the stimulator is adapted to configure the stimulation to cause increased clearance of the fluid from the anterior chamber so as to lower an intraocular pressure of the eye, so as to treat the eye condition.

There is also provided, in accordance with an embodiment of the present invention, apparatus for diagnosing a condition of an eye of a subject, including a stimulator for stimulating at least one site of the subject, configured so that molecular passage increases between the eye of the subject and a tissue of the subject responsive to the stimulation, so as to enable diagnosis of the eye condition, the site selected from the list consisting of: a sphenopalatine ganglion (SPG) of the subject, an anterior ethmoidal nerve of the subject, a posterior ethmoidal nerve of the subject, a communicating branch between an anterior ethmoidal nerve and a retro-orbital branch of an SPG of the subject, a communicating branch between a posterior ethmoidal nerve and a retro-orbital branch of an SPG of the subject, a greater palatine nerve of the subject, a lesser palatine nerve of the subject, a sphenopalatine nerve of the subject, a communicating branch between a maxillary nerve and an SPG of the subject, a nasopalatine nerve of the subject, a posterior nasal nerve of the subject, an infraorbital nerve of the subject, an otic ganglion of the subject, an afferent fiber going into the otic ganglion of the subject, an efferent fiber going out of the otic ganglion of the subject, a vidian nerve of the subject, a greater superficial petrosal nerve of the subject, and a lesser deep petrosal nerve of the subject.

In an embodiment, the tissue includes a systemic blood circulation of the subject, and the stimulator is adapted to configure the stimulation of the site to cause an increase in molecular passage between the eye and the systemic blood circulation.

In an embodiment, the stimulator is adapted to configure the stimulation of the site to cause an increase in molecular passage of a constituent of the eye, from the eye to the tissue.

In an embodiment, the stimulator is adapted to configure the stimulation of the site to cause the increase in molecular passage of the constituent, the constituent selected from the group consisting of: a protein, a hormone, an antibody, an electrolyte, a neuropeptide, and an enzyme.

In an embodiment, the stimulator is adapted to configure the stimulation of the site to cause an increase in molecular passage, from the tissue to at least a portion of the eye, of an agent for facilitating a diagnostic procedure.

In an embodiment, the apparatus includes a sensor, adapted to measure an intraocular pressure of the eye.

There is further provided, in accordance with an embodiment of the present invention, apparatus for treating a condition of a subject, including an electrical stimulator for stimulating at least one stimulation site of the subject, so as to treat the condition, the stimulator adapted to be implanted at an implantation site in or adjacent to an orbital cavity of the subject, the stimulation site selected from the list consisting of: a sphenopalatine ganglion (SPG) of the subject, an anterior ethmoidal nerve of the subject, a posterior ethmoidal nerve of the subject, a communicating branch between an anterior ethmoidal nerve and a retro-orbital branch of an SPG of the subject, a communicating branch between a posterior ethmoidal nerve and a retro-orbital branch of an SPG of the subject, a greater palatine nerve of the subject, a lesser palatine nerve of the subject, a sphenopalatine nerve of the subject, a communicating branch between a maxillary nerve and an SPG of the subject, a nasopalatine nerve of the subject, a posterior nasal nerve of the subject, an infraorbital nerve of the subject, an otic ganglion of the subject, an afferent fiber going into the otic ganglion of the subject, an efferent fiber going out of the otic ganglion of the subject, a vidian nerve of the subject, a greater superficial petrosal nerve of the subject, and a lesser deep petrosal nerve of the subject.

In an embodiment, the apparatus includes at least one electrode, adapted to be implanted in a vicinity of an ethmoidal nerve of the subject.

There is still further provided, in accordance with an embodiment of the present invention, a method for treating a condition of an eye of a subject, including stimulating at least one site of the subject, so as to treat the eye condition, the site selected from the list consisting of: a sphenopalatine ganglion (SPG) of the subject, an anterior ethmoidal nerve of the subject, a posterior ethmoidal nerve of the subject, a communicating branch between an anterior ethmoidal nerve and a retro-orbital branch of an SPG of the subject, a communicating branch between a posterior ethmoidal nerve and a retro-orbital branch of an SPG of the subject, a greater palatine nerve of the subject, a lesser palatine nerve of the subject, a sphenopalatine nerve of the subject, a communicating branch between a maxillary nerve and an SPG of the subject, a nasopalatine nerve of the subject, a posterior nasal nerve of the subject, an infraorbital nerve of the subject, an otic ganglion of the subject, an afferent fiber going into the otic ganglion of the subject, an efferent fiber going out of the otic ganglion of the subject, a vidian nerve of the subject, a greater superficial petrosal nerve of the subject, and a lesser deep petrosal nerve of the subject.

There is additionally provided, in accordance with an embodiment of the present invention, a method for diagnosing a condition of an eye of a subject, including:

stimulating at least one site of the subject, the site selected from the list consisting of: a sphenopalatine ganglion (SPG) of the subject, an anterior ethmoidal nerve of the subject, a posterior ethmoidal nerve of the subject, a communicating branch between an anterior ethmoidal nerve and a retro-orbital branch of an SPG of the subject, a communicating branch between a posterior ethmoidal nerve and a retro-orbital branch of an SPG of the subject, a greater palatine nerve of the subject, a lesser palatine nerve of the subject, a sphenopalatine nerve of the subject, a communicating branch between a maxillary nerve and an SPG of the subject, a nasopalatine nerve of the subject, a posterior nasal nerve of the subject, an infraorbital nerve of the subject, an otic ganglion of the subject, an afferent fiber going into the otic ganglion of the subject, an efferent fiber going out of the otic ganglion of the subject, a vidian nerve of the subject, a greater superficial petrosal nerve of the subject, and a lesser deep petrosal nerve of the subject; and configuring the stimulation so that molecular passage increases between the eye and a tissue of the subject responsive to the stimulation, so as to enable diagnosis of the eye condition.

There is yet additionally provided, in accordance with an embodiment of the present invention, a method for treating a condition of a subject, including:

implanting an electrical stimulator at an implantation site in or adjacent to an orbital cavity of the subject; and driving the electrical stimulator to stimulate at least one stimulation site of the subject, so as to treat the condition, the stimulation site selected from the list consisting of: a sphenopalatine ganglion (SPG) of the subject, an anterior ethmoidal nerve of the subject, a posterior ethmoidal nerve of the subject, a communicating branch between an anterior ethmoidal nerve and a retro-orbital branch of an SPG of the subject, a communicating branch between a posterior ethmoidal nerve and a retro-orbital branch of an SPG of the subject, a greater palatine nerve of the subject, a lesser palatine nerve of the subject, a sphenopalatine nerve of the subject, a communicating branch between a maxillary nerve and an SPG of the subject, a nasopalatine nerve of the subject, a posterior nasal nerve of the subject, an infraorbital nerve of the subject, an otic ganglion of the subject, an afferent fiber going into the otic ganglion of the subject, an efferent fiber going out of the otic ganglion of the subject, a vidian nerve of the subject, a greater superficial petrosal nerve of the subject, and a lesser deep petrosal nerve of the subject.

The present invention will be more fully understood from the following detailed description of the preferred embodiments thereof, taken together with the drawings, in which:

DETAILED DESCRIPTION OF THE INVENTION

Figure 1:
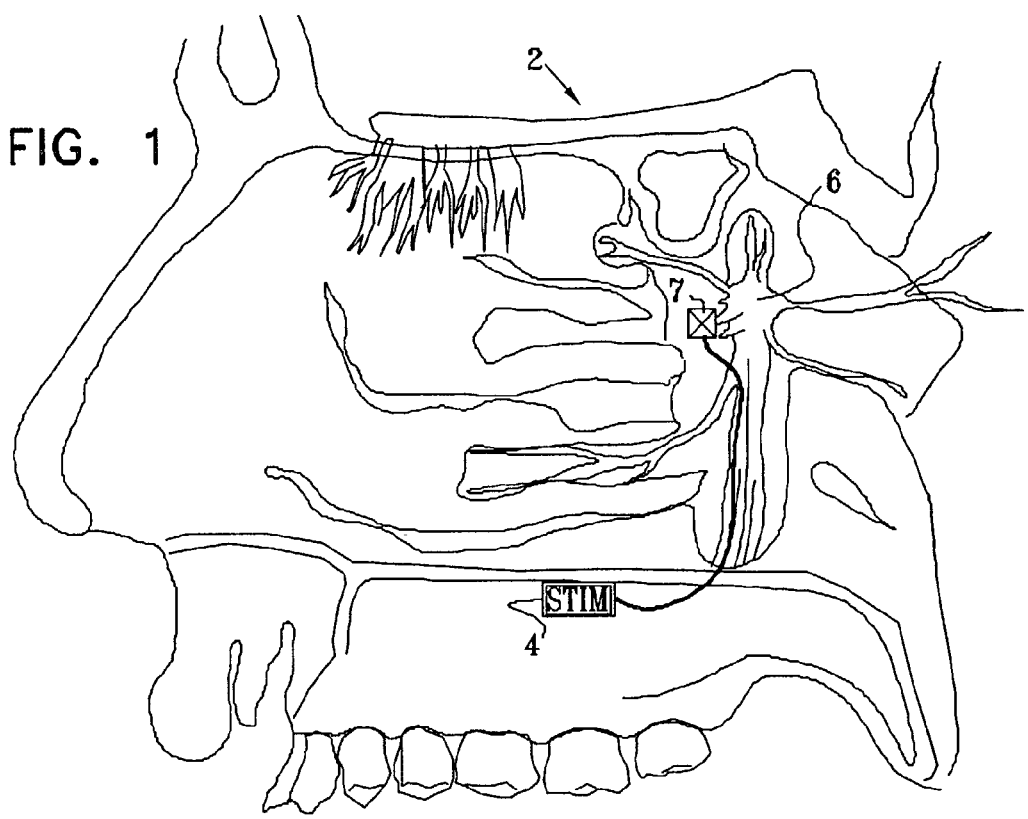
FIG. 1 is a schematic pictorial view of a fully implantable stimulator for stimulation of an MTS, in accordance with a preferred embodiments of the present invention.

FIG. 1 is a schematic pictorial view of a fully-implantable stimulator 4, for stimulation of a "modulation target site" (MTS), as defined hereinbelow, such as a sphenopalatine ganglion (SPG) 6, in accordance with a preferred embodiments of the present invention. In FIG. 1, a human nasal cavity 2 is shown, and stimulator 4 is implanted between the hard palate and the mucoperiosteum (not shown) of the roof of the mouth. Branches of parasympathetic neurons coming from SPG 6 extend to the middle cerebral and anterior cerebral arteries (not shown). Preferably, one or more relatively short electrodes 7 extend from stimulator 4 to contact or to be in a vicinity of an MTS, such as SPG 6.

In the present patent application and the claims, a "modulation target site" consists of:

a sphenopalatine ganglion (SPG) (also called a pterygopalatine ganglion);

an anterior ethmoidal nerve;

a posterior ethmoidal nerve;

a communicating branch between the anterior ethmoidal nerve and the SPG (retro orbital branch);

a communicating branch between the posterior ethmoidal nerve and the SPG (retro orbital branch)

a nerve of the pterygoid canal (also called a vidian nerve), such as a greater superficial petrosal nerve (a preganglionic parasympathetic nerve) or a lesser deep petrosal nerve (a postganglionic sympathetic nerve);

a greater palatine nerve;

a lesser palatine nerve;

a sphenopalatine nerve;

a communicating branch between the maxillary nerve and the sphenopalatine ganglion;

a nasopalatine nerve;

a posterior nasal nerve;

an infraorbital nerve;

an otic ganglion;

an afferent fiber going into the otic ganglion; and/or an efferent fiber going out of the otic ganglion.

For some applications, stimulator 4 is implanted on top of the bony palate, in the bottom of the nasal cavity. Alternatively or additionally, the stimulator is implanted at the lower side of the bony palate, at the top of the oral cavity. In this instance, one or more flexible electrodes 7 originating in the stimulator are passed through the palatine bone or posterior to the soft palate, so as to be in a position to stimulate the SPG or another MTS. Further alternatively or additionally, the stimulator may be directly attached to the SPG and/or to another MTS.

For some applications, stimulator 4 is delivered to a desired point within nasal cavity 2 by removably attaching stimulator 4 to the distal end of a rigid or slightly flexible introducer rod (not shown) and inserting the rod into one of the patient's nasal passages until the stimulator is properly positioned. As appropriate, the placement process may be facilitated by fluoroscopy, x-ray guidance, fine endoscopic surgery (FES) techniques or by any other effective guidance method known in the art, or by combinations of the aforementioned. Preferably, the ambient temperature and/or cerebral blood flow is measured concurrently with insertion. The cerebral blood flow may be measured with, for example, a laser Doppler unit positioned at the patient's forehead or transcranial Doppler measurements. Verification of proper implantation of the electrodes onto the appropriate neural structure may be performed by activating the device, and generally simultaneously monitoring cerebral blood flow.

The passage of certain molecules from cerebral blood vessels into the brain is hindered by the BBB. The endothelium of the capillaries, the plasma membrane of the blood vessels, and the foot processes of the astrocytes all impede uptake by the brain of the molecules. The BBB generally allows only small molecules (e.g., hydrophilic molecules of molecular weight less than about 200 Da, and lipophilic molecules of less than about 500 Da) to pass from the circulation into the brain.

As used in the present application and in the claims, the BBB comprises the tight junctions opposing the passage of most ions and large molecular weight compounds from the blood to brain tissue, as well as from the blood to structures of the eye.

In accordance with a preferred embodiment of the present invention, parasympathetic activation induced by current from stimulator 4 overcomes the resistance to trans-BBB molecular movement generated by the endothelium of the cerebral capillaries and the plasma membrane. For some applications, therefore, stimulator 4 may be used to transiently remove a substantial obstacle to the passage of drugs from the blood to the eye, thereby facilitating transport of drugs to a tissue of the eye. For example, the stimulator may cyclically apply current for about two minutes, and subsequently have a rest period of between about 1 and 20 minutes.

It is hypothesized that two neurotransmitters play an important role in this change in properties of the BBB—vasoactive intestinal polypeptide (VIP) and nitric oxide (NO). (Acetylcholine may also be involved.) VIP is a short peptide, and NO is a gaseous molecule. VIP is believed to be a major factor in facilitating plasma protein extravasation (PPE), while NO is responsible for vasodilation. For some applications, stimulator 4 is adapted to vary parameters of the current applied to an MTS, as appropriate, in order to selectively influence the activity of one or both of these neurotransmitters. For example, stimulation of the parasympathetic nerve at different frequencies can induce differential secretion—low frequencies cause secretion of NO, while high frequencies (e.g., above about 10 Hz) cause secretion of peptides (VIP).

For other applications, a constant level DC signal, or a slowly varying voltage ramp is applied, in order to block parasympathetic neural activity in affected tissue. Alternatively, similar results can be obtained by stimulating at a rate higher than about 10 Hz, because this tends to exhaust neurotransmitters. Thus, stimulator 4 may be configured to induce parasympathetic electrical block, in order to cause vasoconstriction by mimicking the overall effect of chemical block on the SPG.

Figure 2:
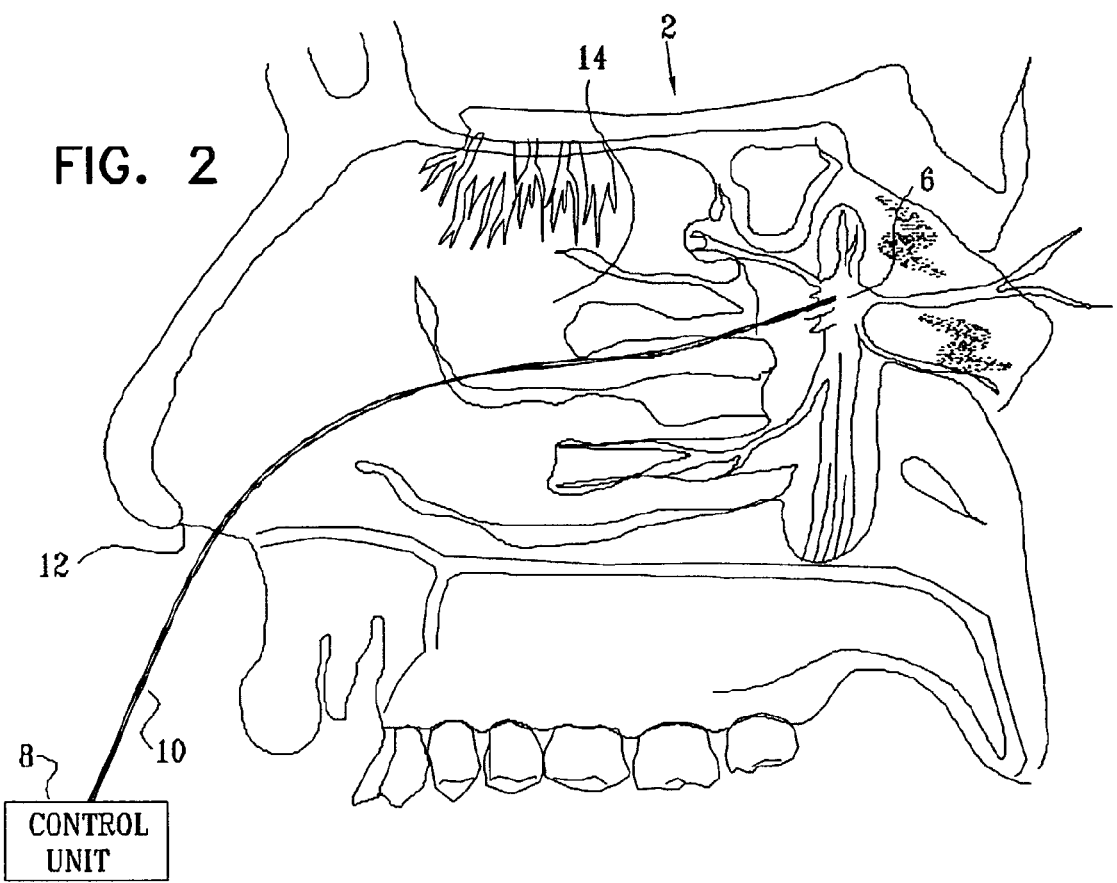
FIG. 2 is a schematic pictorial view of another stimulator for stimulation of an MTS, in accordance with a preferred embodiment of the present invention.

FIG. 2 is a schematic illustration of a stimulator control unit 8 positioned external to a patient's body, in accordance with a preferred embodiment of the present invention. At least one flexible electrode 10 preferably extends from control unit 8, through a nostril 12 of the patient, and to a position within the nasal cavity 14 that is adjacent to SPG 6.

It is to be understood that electrodes 7 (FIG. 1) and 10 may each comprise one or more electrodes, e.g., two electrodes, or an array of microelectrodes. For applications in which stimulator 4 comprises a metal housing that can function as an electrode, then typically one electrode 7 is used, operating in a monopolar mode. Regardless of the total number of electrodes in use, typically only a single or a double electrode extends to SPG 6. Other electrodes 7 or 10 or a metal housing of stimulator 4 are preferably temporarily or permanently implanted in contact with other parts of nasal cavity 2.

Each of electrodes 7 and/or 10 preferably comprises a suitable conductive material, for example, a physiologically-acceptable material such as silver, iridium, platinum, a platinum iridium alloy, titanium, nitinol, or a nickel-chrome alloy. For some applications, one or more of the electrodes have lengths ranging from about 1 to 5 mm, and diameters ranging from about 50 to 100 microns. Each electrode is preferably insulated with a physiologically-acceptable material such as polyethylene, polyurethane, or a co-polymer of either of these. The electrodes are preferably spiral in shape, for better contact, and may have a hook shaped distal end for hooking into or near the SPG. Alternatively or additionally, the electrodes may comprise simple wire electrodes, spring-loaded "crocodile" electrodes, or adhesive probes, as appropriate.

In a preferred embodiment of the invention, each one of electrodes 7 and/or 10 comprises a substantially smooth surface, except that the distal end of each such electrode is configured or treated to have a large surface area. For example, the distal tip may be porous platinized. Alternatively or additionally, at least the tip of electrode 7 or 10, and/or a metal housing of stimulator 4 includes a coating comprising an anti-inflammatory drug, such as beclomethasone sodium phosphate or beclomethasone phosphate. Alternatively, such an anti-inflammatory drug is injected or otherwise applied.

Figure 3:
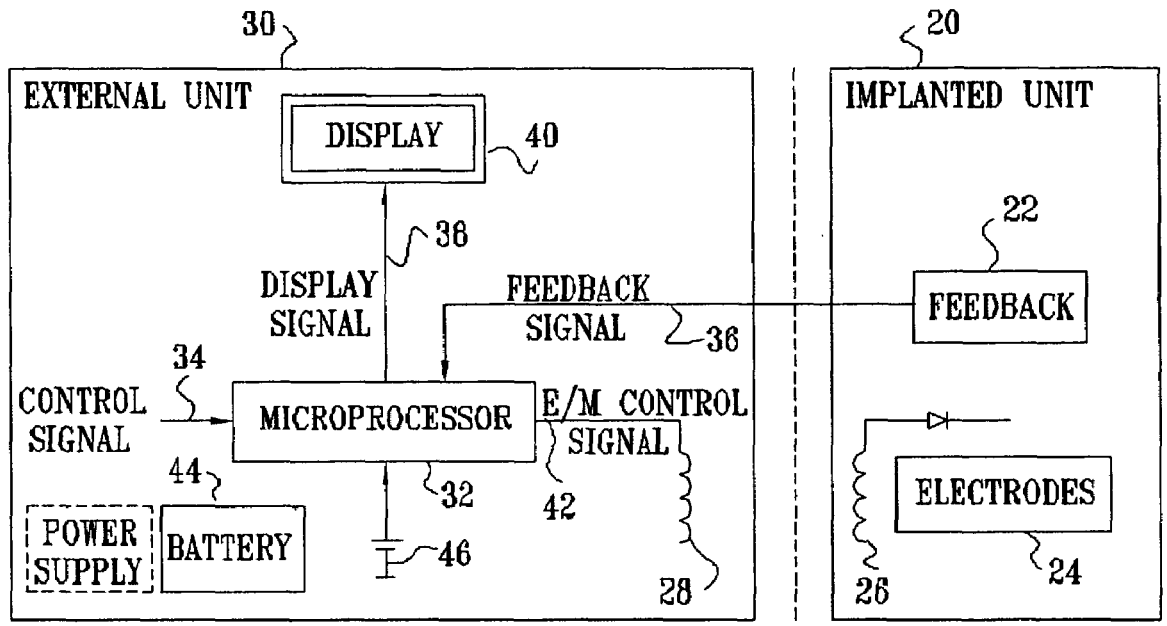
FIG. 3 is a schematic block diagram illustrating circuitry for use with the stimulator shown in FIG. 1, in accordance with a preferred embodiment of the present invention.

FIG. 3 is a schematic block diagram illustrating circuitry comprising an implanted unit 20 and an external unit 30, for use with stimulator 4 (FIG. 1), in accordance with a preferred embodiment of the present invention. Implanted unit 20 preferably comprises a feedback block 22 and one or more sensing or signal application electrodes 24. Implanted unit 20 typically also comprises an electromagnetic coupler 26, which receives power and/or sends or receives data signals to or from an electromagnetic coupler 28 in external unit 30.

External unit 30 preferably comprises a microprocessor 32 which receives an external control signal 34 (e.g., from a physician or from the patient), and a feedback signal 36 from feedback block 22. Control signal 34 may include, for example, operational parameters such as a schedule of operation, patient parameters such as the patient's weight, or signal parameters, such as desired frequencies or amplitudes of a signal to be applied to an MTS. If appropriate, control signal 34 can comprise an emergency override signal, entered by the patient or a healthcare provider to terminate stimulation or to modify it in accordance with a predetermined program. Microprocessor 32, in turn, preferably processes control signal 34 and feedback signal 36 so as to determine one or more parameters of the electric current to be applied through electrodes 24. Responsive to this determination, microprocessor 32 typically generates an electromagnetic control signal 42 that is conveyed by electromagnetic coupler 28 to electromagnetic coupler 26. Control signal 42 preferably corresponds to a desired current or voltage to be applied by electrodes 24 to an MTS, such as SPG 6, and, in a preferred embodiment, inductively drives the electrodes. The configuration of couplers 26 and 28 and/or other circuitry in units 20 or 30 may determine the intensity, frequency, shape, monophasic or biphasic mode, or DC offset of the signal (e.g., a series of pulses) applied to designated tissue.

Power for microprocessor 32 is typically supplied by a battery 44 or, optionally, another DC power supply. Grounding is provided by battery 44 or a separate ground 46. If appropriate, microprocessor 32 generates a display signal 38 that drives a display block 40 of external unit 30. Typically, but not necessarily, the display is activated to show feedback data generated by feedback block 22, or to provide a user interface for the external unit.

Implanted unit 20 is preferably packaged in a case made of titanium, platinum or an epoxy or other suitable biocompatible material. Should the case be made of metal, then the case may serve as a ground electrode and, therefore, stimulation typically is performed in a monopolar mode. Alternatively, should the case be made of biocompatible plastic material, two electrodes 24 are typically driven to apply current to the MTS.

For some applications, the waveform applied by one or more of electrodes 24 to designated tissue of an MTS (e.g., the SPG) comprises a waveform with an exponential decay, a ramp up or down, a square wave, a sinusoid, a saw tooth, a DC component, or any other shape known in the art to be suitable for application to tissue. Alternatively or additionally, the waveform comprises one or more bursts of short shaped or square pulses—each pulse preferably less than about 1 ms in duration. Generally, appropriate waveforms and parameters thereof are determined during an initial test period of external unit 30 and implanted unit 20. For some applications, the waveform is dynamically updated according to measured physiological parameters, measured during a period in which unit 20 is stimulating an MTS, and/or during a non-activation (i.e., standby) period.

Figure 4:
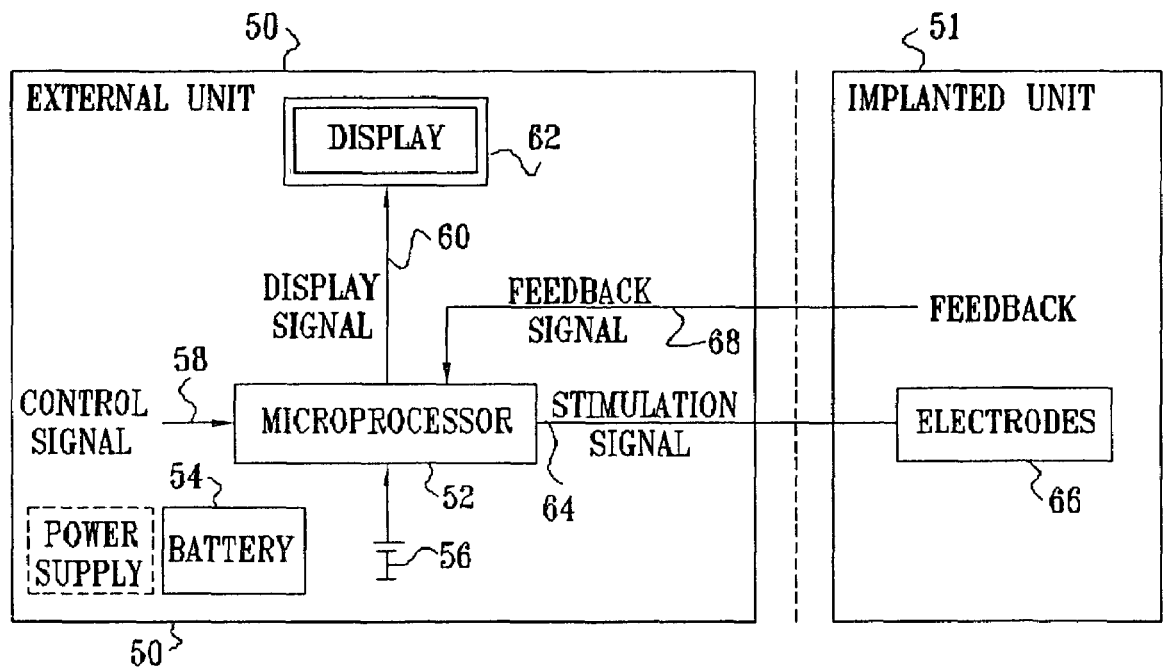
FIG. 4 is a schematic block diagram illustrating circuitry for use with the stimulator shown in FIG. 2, in accordance with a preferred embodiment of the present invention.

FIG. 4 is a schematic block diagram of circuitry for use, for example, in conjunction with control unit 8 (FIG. 2), in accordance with a preferred embodiment of the present invention. An external unit 50 comprises a microprocessor 52 supplied by a battery 54 or another DC power source. Grounding may be provided by battery 54 or by a separate ground 56. Microprocessor 52 preferably receives control and feedback signals 58 and 68 (analogous to signal 34 and 36 described hereinabove), and generates responsive thereto a stimulation signal 64 conveyed by one or more electrodes 66 to an MTS or other tissue. Typically, but not necessarily, feedback signal 68 comprises electrical feedback measured by one or more of electrodes 66 and/or feedback from other sensors on or in the patient's brain or elsewhere coupled to the patient's body. If appropriate, microprocessor 52 generates a display signal 60 which drives a display block 62 to output relevant data to the patient or the patient's physician. Typically, some or all of electrodes 66 are temporarily implanted in the patient (e.g., following a stroke), and are directly driven by wires connecting the external unit to the implanted unit.

Figure 5A:
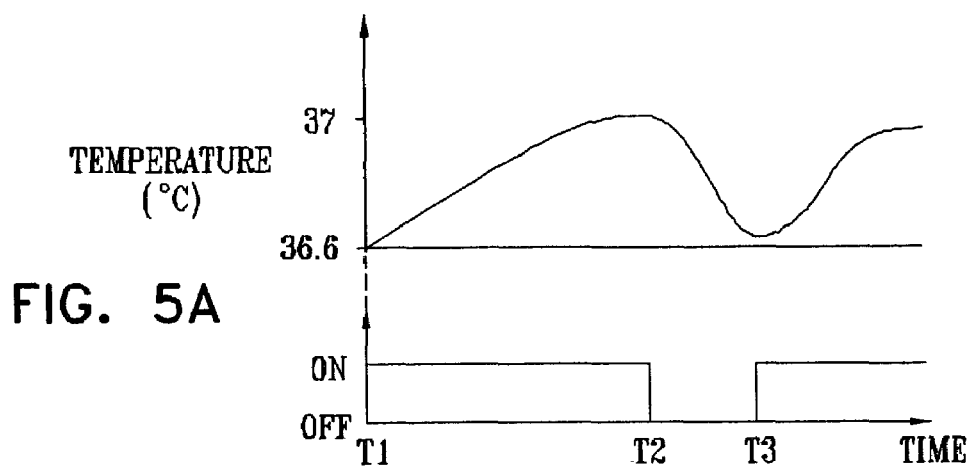
FIGS. 5A and 5B are schematic illustrations depicting different modes of operation of stimulators such as those shown in FIGS. 1 and 2, in accordance with preferred embodiments of the present invention.

FIG. 5A is a graph schematically illustrating a mode of operation of one or more of the devices shown in FIGS. 1–4, in accordance with a preferred embodiment of the present invention. Preferably, the effect of the applied stimulation is monitored by means of a temperature transducer at an MTS (e.g., the SPG) or elsewhere in the head, e.g., in the nasal cavity. As shown in FIG. 5A for a step (ON/OFF) mode of stimulation, stimulation of an MTS or related tissue is initiated at a time T1, and this is reflected by a measurable rise in temperature (due to increased blood flow). Once the temperature rises to a predetermined or dynamically-varying threshold (e.g., 37° C.), stimulation is terminated (time T2), responsive to which the temperature falls. As appropriate, when the temperature drops to a designated or dynamically-determined point, the stimulation is reinitiated (time T3). Preferably, suitable temperatures or other physiological parameters are determined for each patient so as to provide the optimal treatment. If appropriate, control instructions may also be received from the patient.

Figure 5B:
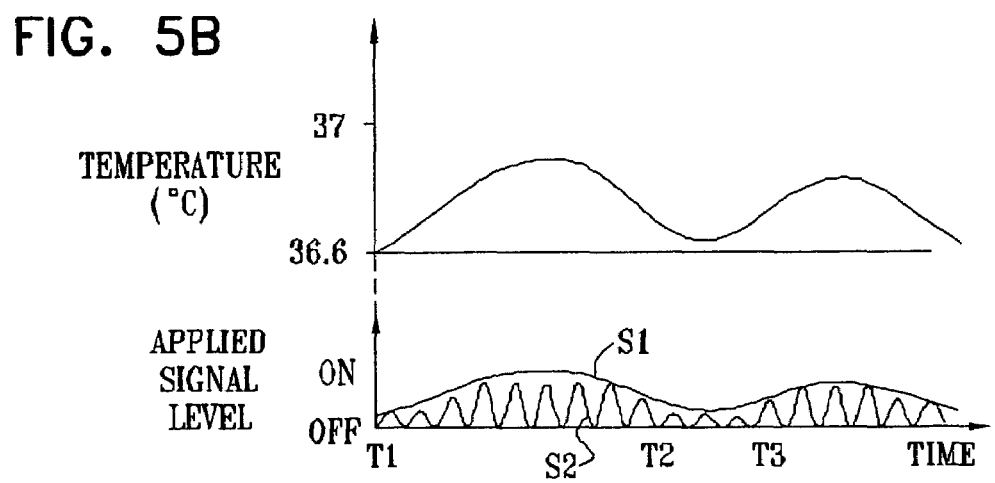

FIG. 5B is a graph schematically illustrating a mode of operation of one or more of the devices shown in FIGS. 1–4, in accordance with another preferred embodiment of the present invention. In this embodiment, the amplitude of the waveform applied to an MTS is varied among a continuous set of values (S1), or a discrete set of values (S2), responsive to the measured temperature, in order to achieve the desired performance. It will be appreciated that other feedback parameters measured in the head (e.g., intraocular pressure, intracranial pressure and/or cerebral blood flow), as well as measured systemic parameters (e.g., heart rate) and subjective patient inputs may be used in conjunction with or separately from temperature measurements, in order to achieve generally optimal performance of the implanted apparatus.

Figure 6:
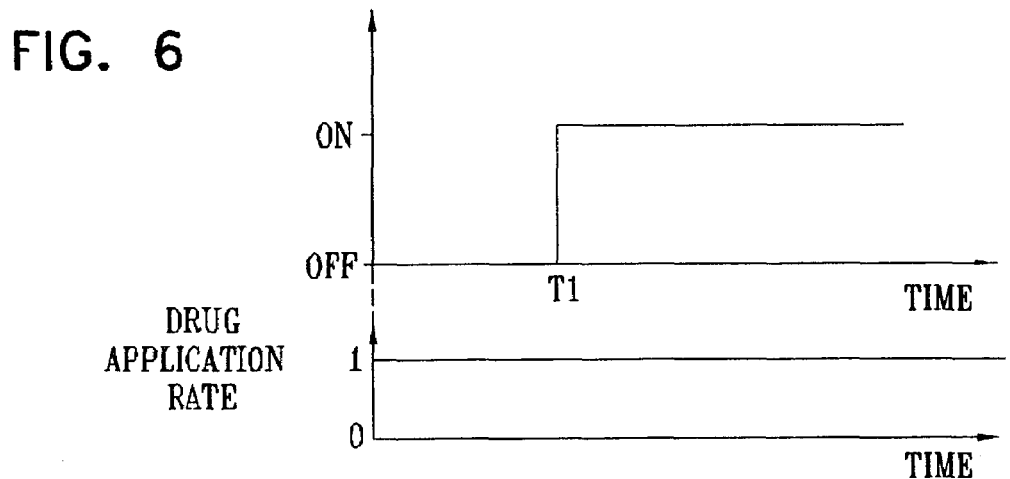
FIG. 6 is a schematic illustration of a mode of operation of the stimulators shown in FIGS. 1 and 2, synchronized with a drug delivery system, in accordance with a preferred embodiment of the present invention.

FIG. 6 is a graph schematically illustrating a mode of operation of one or more of the devices shown in FIGS. 1–4, 14, and 15, in accordance with a preferred embodiment of the present invention. In this embodiment, a drug is administered to the patient at a constant rate, e.g., intravenously, prior to the initiation of chemical, mechanical, electrical and/or odorant stimulation of an MTS at time T1. Advantageously, this prior generation of heightened concentrations of the drug in the blood tends to provide relatively rapid transfer of the drug across the BBB and into the eye via the brain, without unnecessarily prolonging the enhanced permeability of the BBB while waiting for the blood concentration of the drug to reach an appropriate level. Alternatively, for some applications it is desirable to give a single injection of a bolus of the drug shortly before or after initiation of stimulation of an MTS. Typically, combined administration and stimulation schedules are determined by the patient's physician based on the biochemical properties of each drug targeted at the eye.

Figure 7:
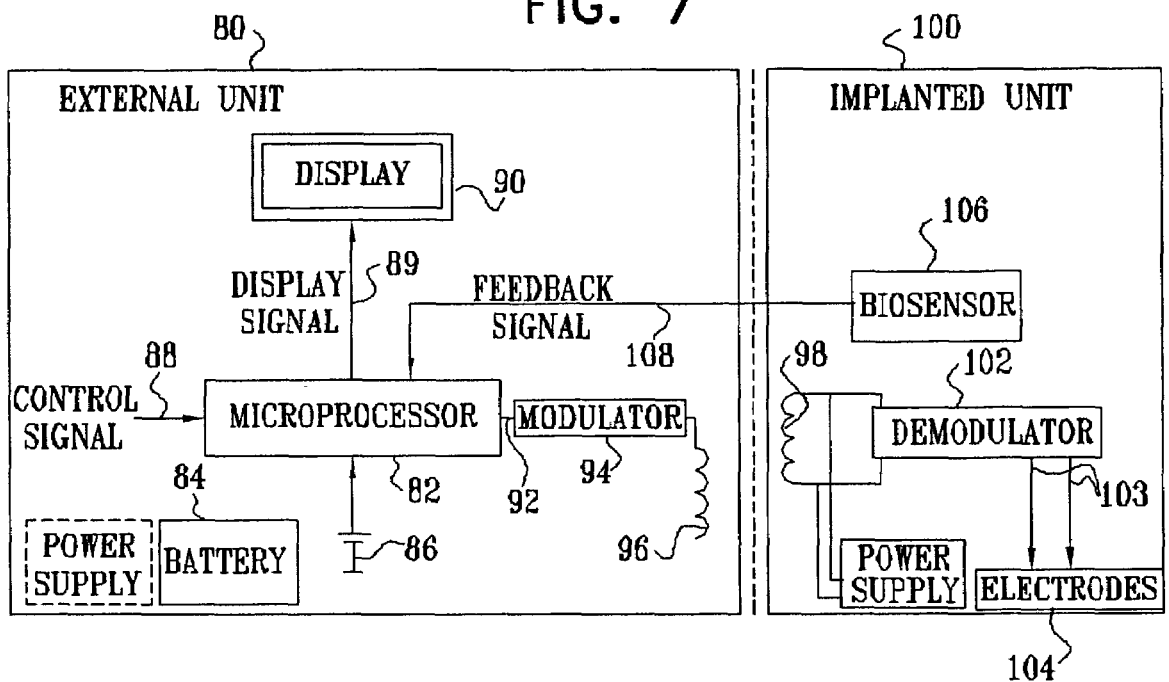
FIG. 7 is a schematic block diagram illustrating circuitry for use with the stimulator shown in FIG. 1, where the stimulator is driven by an external controller and energy source using a modulator and a demodulator, in accordance with a preferred embodiment of the present invention.

FIG. 7 is a schematic block diagram showing circuitry for parasympathetic stimulation, which is particularly useful in combination with the embodiment shown in FIG. 1, in accordance with a preferred embodiment of the present invention. An external unit 80 preferably comprises a microprocessor 82 that is powered by a battery 84 and/or an AC power source. Microprocessor 82 is grounded through battery 84 or through an optional ground 86.

In a typical mode of operation, an external control signal 88 is input to microprocessor 82, along with a feedback signal 108 from one or more biosensors 106, which are typically disposed in a vicinity of an implanted unit 100 or elsewhere on or in the patient's body. Responsive to signals 88 and 108, microprocessor 82 preferably generates a display signal 89 which drives a display 90, as described hereinabove. In addition, microprocessor 82 preferably processes external control signal 88 and feedback signal 108, to determine parameters of an output signal 92, which is modulated by a modulator 94. The output therefrom preferably drives a current through an electromagnetic coupler 96, which inductively drives an electromagnetic coupler 98 of implanted unit 100. A demodulator 102, coupled to electromagnetic coupler 98, in turn, generates a signal 103 which drives at least one electrode 104 to apply current to an MTS or to other tissue, as appropriate.

Preferably, biosensor 106 comprises implantable or external medical apparatus including, for example, one or more of the following:

a blood flow sensor,
a temperature sensor,
a chemical sensor,
an ultrasound sensor,
transcranial Doppler (TCD) apparatus,
laser-Doppler apparatus,
a systemic or intracranial blood pressure sensor (e.g., comprising a piezoelectric crystal or capacitive sensor fixed to a major cerebral blood vessel, capable of detecting a sudden blood pressure increase indicative of a clot), an intraocular pressure sensor, e.g., comprising a piezoelectric crystal or capacitive sensor coupled to the nasal (medial) wall of the orbit, or at another site suitable for measuring intraocular pressure, a tissue vitality sensor, e.g., comprising laser Doppler or other optical apparatus for detecting a NAD/NADH ratio in tissue, using optical techniques known in the art for detecting the metabolic state of a tissue, a kinetics sensor, comprising, for example, an acceleration, velocity, or level sensor (e.g., a mercury switch), for indicating body dispositions such as a sudden change in body attitude (as in collapsing), an electroencephalographic (EEG) sensor comprising EEG electrodes attached to, or implanted in, the patients head, for indicating changes in neurological patterns, such as symptoms of stroke, a blood vessel clot detector (e.g., as described hereinbelow with reference to FIG. 13), or other monitors of physiological quantities suitable for carrying out the objects of this or other embodiments of the present invention.

Figure 8:
FIG. 8 depicts sample modulator and demodulator functions for use with the circuitry of FIG. 7, in accordance with a preferred embodiment of the present invention.

FIG. 8 is a schematic illustration showing operational modes of modulator 94 and/or demodulator 102, in accordance with a preferred embodiment of the present invention. The amplitude and frequency of signal 92 in FIG. 7 can have certain values, as represented in the left graph; however, the amplitude and frequency are modulated so that signal 103 has different characteristics.

Figure 9:
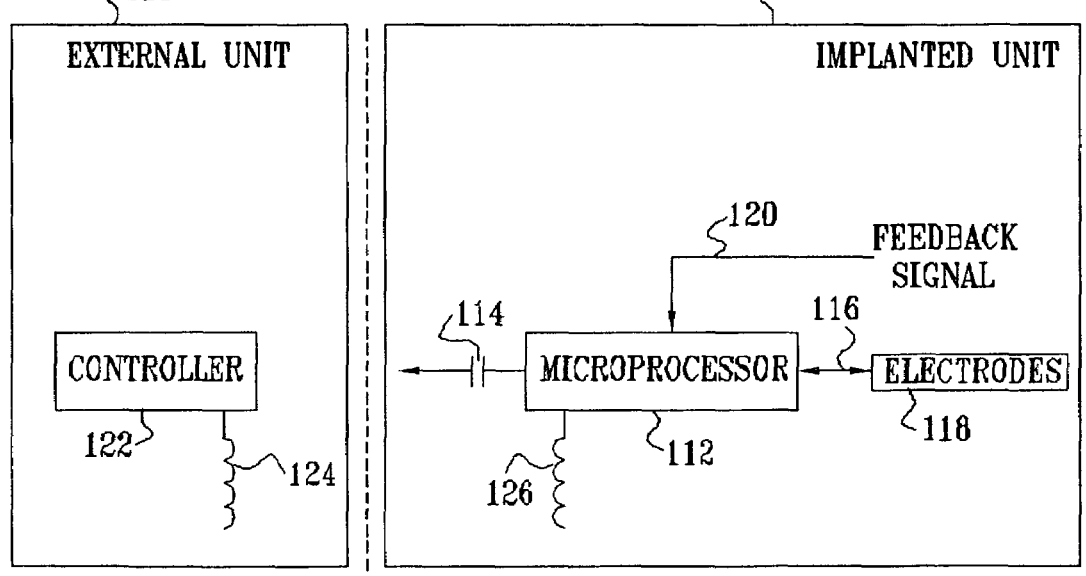
FIGS. 9, 10A, and 10B are schematic diagrams illustrating further circuitry for use with implantable stimulators, in accordance with respective preferred embodiments of the present invention.

FIG. 9 is a schematic illustration of further apparatus for stimulation of an MTS, in accordance with a preferred embodiment of the present invention. In this embodiment, substantially all of the processing and signal generation is performed by circuitry in an implanted unit 110 in the patient, and, preferably, communication with a controller 122 in an external unit 111 is performed only intermittently. The implanted unit 110 preferably comprises a microprocessor 112 coupled to a battery 114. Microprocessor 112 generates a signal 116 that travels along at least one electrode 118 to stimulate the MTS. A feedback signal 120 from a biosensor (not shown) and/or from electrode 118 is received by microprocessor 112, which is adapted to modify stimulation parameters responsive thereto. Preferably, microprocessor 112 and controller 122 are operative to communicate via wireless couplers 126 and 124 (e.g., electromagnetic couplers), in order to exchange data or to change parameters. Further preferably, battery 114 is wirelessly rechargeable (e.g., inductively rechargeable by electromagnetic coupling).

Figure 10A:
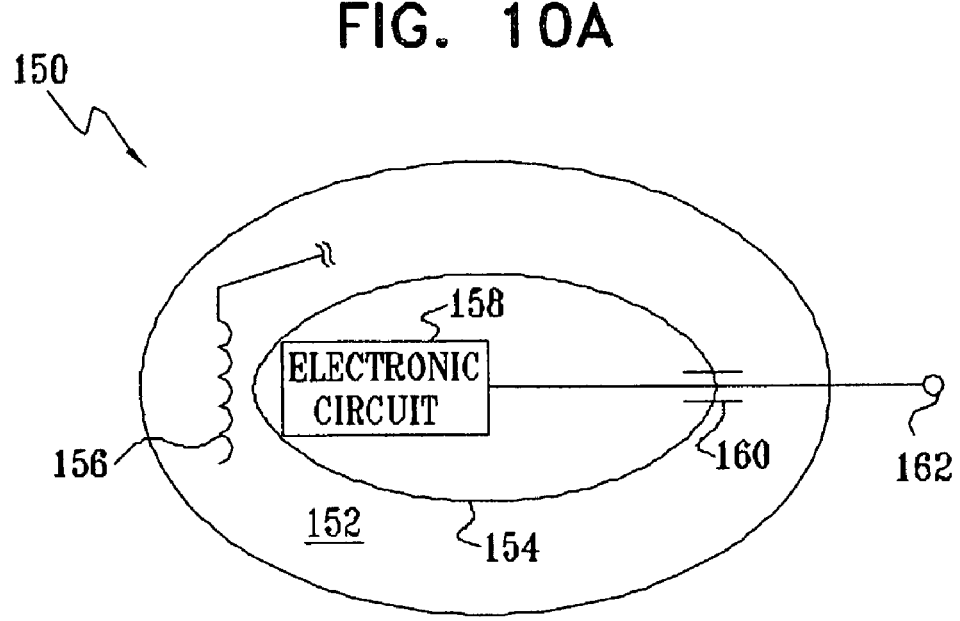

FIG. 10A is a schematic illustration of a stimulator 150, in accordance with a preferred embodiment of the present invention. Preferably, substantially all of the electronic components (including an electronic circuit 158 having a rechargeable energy source) are encapsulated in a biocompatible metal case 154. An inductive coil 156 and at least one electrode 162 are preferably coupled to circuit 158 by means of a feed-through coupling 160. The inductive coil is preferably isolated by an epoxy coating 152, which allows for higher efficiency of the electromagnetic coupling.

Figure 10B:
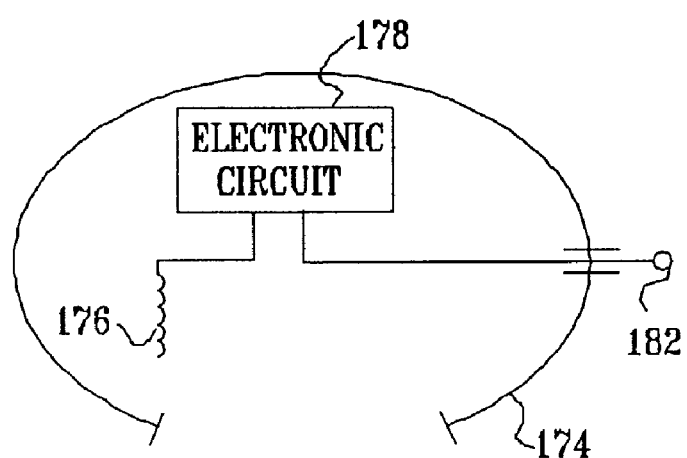
Figure 10B:

FIG. 10B is a schematic illustration of another configuration of an implantable stimulator, in accordance with a preferred embodiment of the present invention. Preferably, substantially all of the electronic components (including an inductive coil 176 and an electronic circuit 178 having a rechargeable energy source) are encapsulated in a biocompatible metal case 174. One or more feed-throughs are preferably provided to enable coupling between at least one electrode 182 and the electronic circuit, as well as between inductive coil 176 and another inductive coil (not shown) in communication therewith.

With reference to FIGS. 10A and 10B, the energy source for electronic circuits 158 and 178 may comprise, for example, a primary battery, a rechargeable battery, or a super capacitor. For applications in which a rechargeable battery or a super capacitor is used, any kind of energizing means may be used to charge the energy source, such as (but not limited to) standard means for inductive charging or a miniature electromechanical energy converter that converts the kinetics of the patient movement into electrical charge. Alternatively, an external light source (e.g., a simple LED, a laser diode, or any other light source) may be directed at a photovoltaic cell in the electronic circuit. Further alternatively, ultrasound energy is directed onto the implanted unit, and transduced to drive battery charging means.

Figure 11:
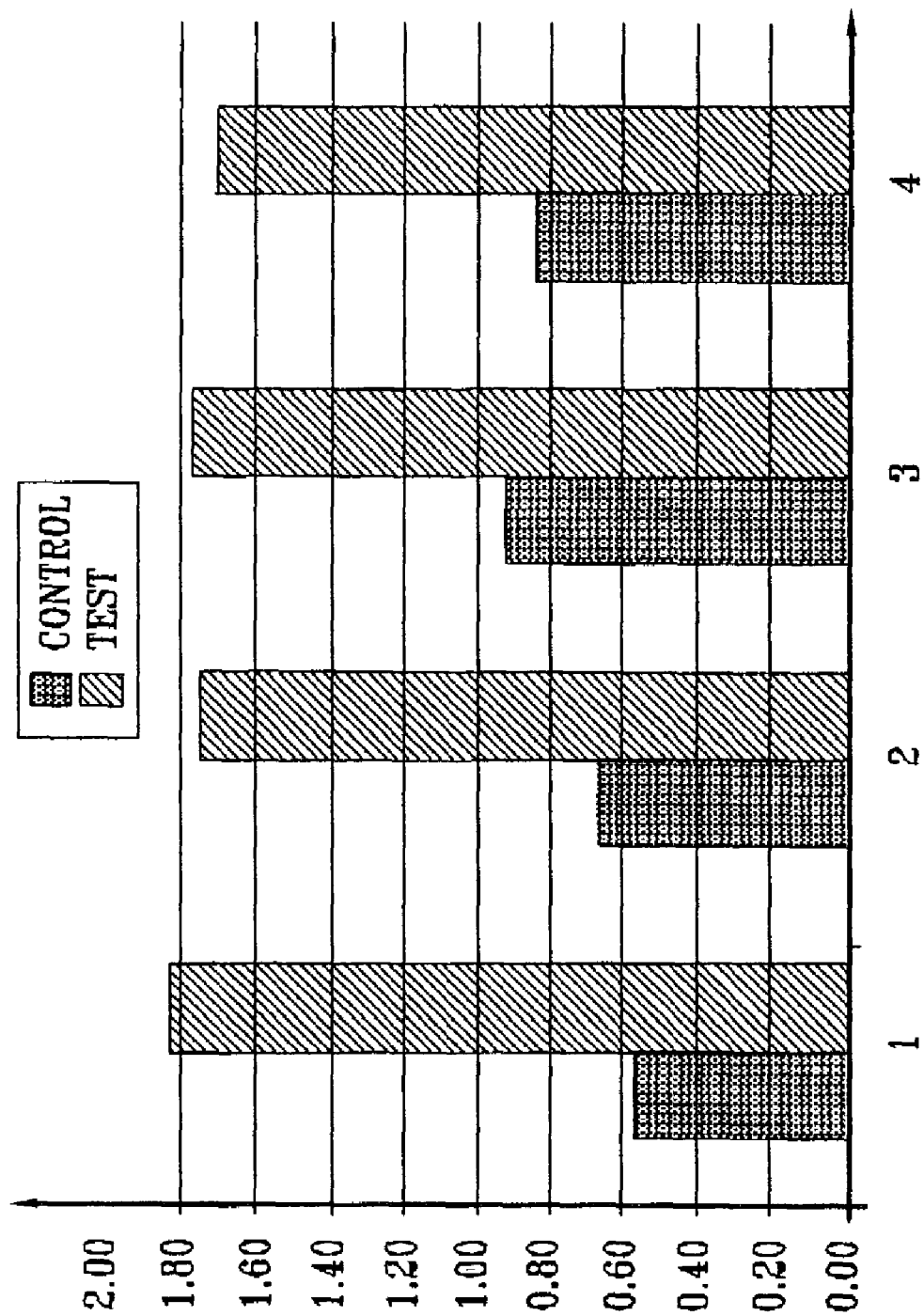
FIGS. 11 and 12 are bar graphs showing experimental data collected in accordance with a preferred embodiment of the present invention.
Figure 12:
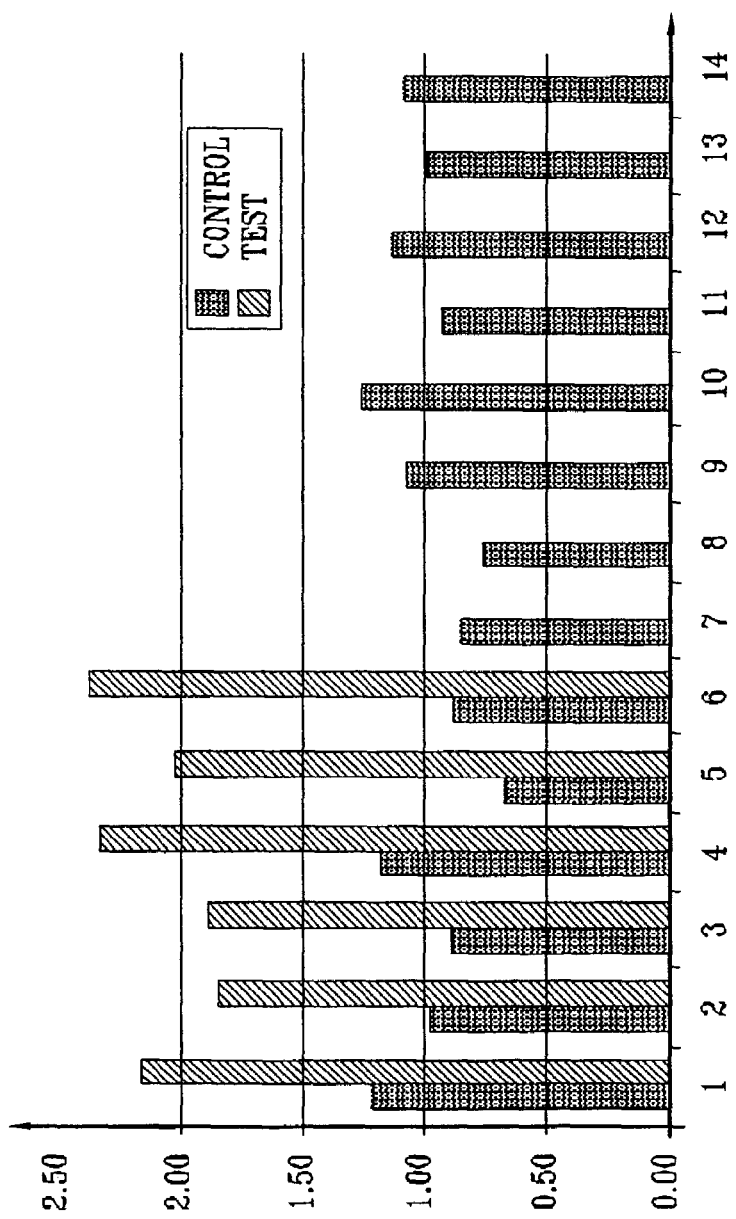

FIGS. 11 and 12 are bar graphs showing experimental results obtained during rat experiments performed in accordance with a preferred embodiment of the present invention. A common technique in monitoring bio-distribution of materials in a system includes monitoring the presence and level of radio-labeled tracers. These tracers are unstable isotopes of common elements (e.g., Tc, In, Cr, Ga, and Gd), conjugated to target materials. The chemical properties of the tracer are used as a predictor for the behavior of other materials with similar physiochemical properties, and are selected based on the particular biological mechanisms that are being evaluated. Typically, a patient or experimental animal is placed on a Gamma camera, or target tissue samples can be harvested and placed separately into a well counter. For the purpose of the present set of experiments which were performed, the well counter method was chosen due to its higher sensitivity and spatial resolution. A series of experiments using 99Tc-DTPA (DTPA molecule conjugated to a 99-Technetium isotope) were performed. The molecular weight of 99Tc-DTPA is 458 Da, its lipophilicity is negative, and its electric charge is +1. These parameters are quite similar with pharmacological agents used in standard chemotherapy, such as tamoxifen, etoposide and irinotecan.

FIGS. 11 and 12 show results obtained using 99Tc-DTPA penetration assays using ordinary brain sampling techniques (FIG. 11) and peeled brain techniques (FIG. 12). The x-axis of each graph represents different experimental runs, and the y-axis of each graph is defined as: [(hemisphere radioactivity)/(hemisphere weight)]/[(total injected radioactivity)/(total animal weight)]. The results obtained demonstrate an average 2.5-fold increase in the penetration of 99Tc-DTPA to the rat brain. It is noted that these results were obtained by unilateral stimulation of the SPG. The inventors believe that bilateral SPG stimulation will approximately double drug penetration, relative to unilateral SPG stimulation.

In both FIG. 11 and FIG. 12, some animals were designated as control animals, and other animals were designated as test animals. In each group, the left and right hemispheres were tested separately, and the height of each bar represents, for a given animal and a given hemisphere, the normalized level of radioactivity as defined above. Thus, FIG. 11 shows results from a total of four test hemispheres and four control hemispheres. FIG. 12 shows results from six test hemispheres and fourteen control hemispheres. The juxtaposition of control and test bars in the bar graphs is not meant to imply pairing of control and test hemispheres.

Figure 13:
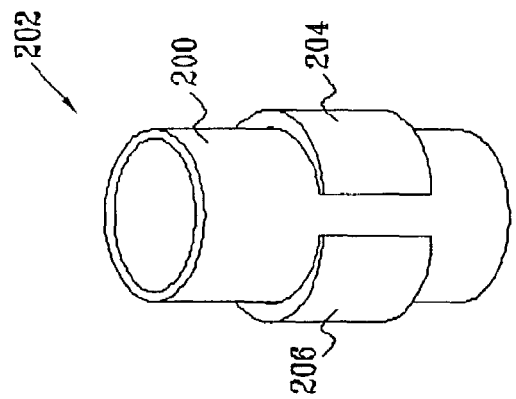
FIG. 13 is a schematic illustration of a sensor for application to a blood vessel, in accordance with a preferred embodiment of the present invention.

FIG. 13 is a schematic illustration of acoustic or optical clot detection apparatus 202, for use, for example, in providing feedback to any of the microprocessors or other circuitry described hereinabove, in accordance with a preferred embodiment of the present invention. The detection is preferably performed by coupling to a major blood vessel 200 (e.g., the internal carotid artery or aorta) a detecting element comprising an acoustic or optical transmitter/receiver 206, and an optional reflecting surface 204. Natural physiological liquids may serve as a mediating fluid between the device and the vessel. Preferably, the transmitter/receiver generates an ultrasound signal or electromagnetic signal which is reflected and returned, and a processor evaluates changes in the returned signal to detect indications of a newly-present clot. Alternatively, a transmitter is placed on side of the vessel and a receiver is placed on the other side of the vessel. In either case, for some applications, more than one such apparatus 202 are placed on the vessel, in order to improve the probability of successful clot detection for possible estimation of the clot's direction of motion within the vessel, and to lower the false alarm (i.e. false detection) rate.

Figure 14:
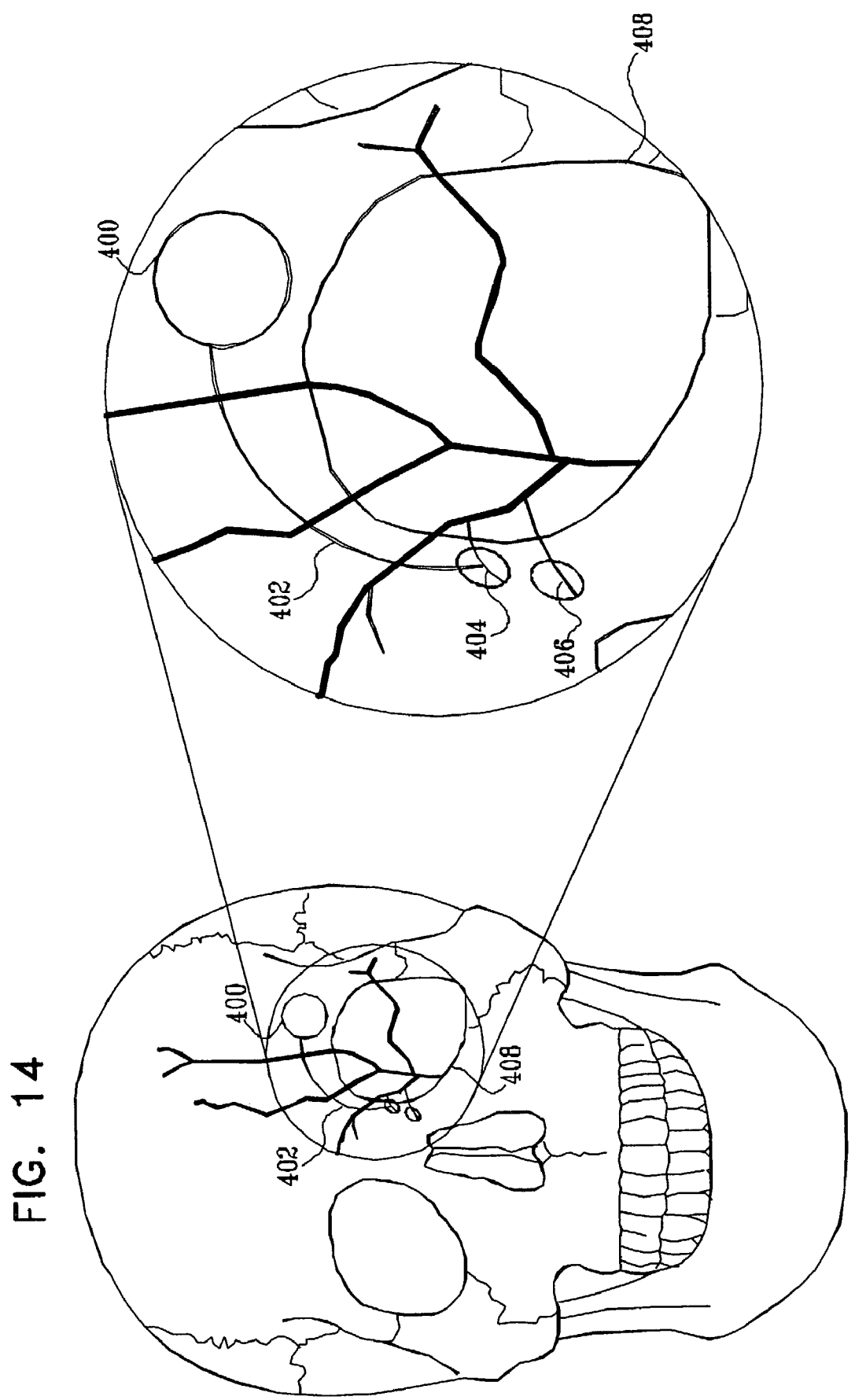
FIG. 14 is a schematic illustration of an implantable stimulator for stimulation of an MTS, in accordance with a preferred embodiments of the present invention.

FIG. 14 is a schematic illustration of an implantable stimulator 400 for stimulation of an MTS, in accordance with a preferred embodiments of the present invention. Stimulator 400 is preferably implanted adjacent to orbital cavity 408 of a subject. At least one electrode 402 extends from the stimulator to at least one of: an anterior ethmoidal nerve 404 and a posterior ethmoidal nerve 406, which are modulation target sites. Stimulator 400 is preferably implanted through an incision made in the upper edge of the eyelid (not shown).

Embodiments of the present invention have many medical applications for treating conditions of the eye. For example, chemotherapeutic drugs can be administered to tissue of the eye via cerebral tissue in order to treat tumors of the eye. Most of the chemotherapeutic drugs have molecular weights of 200–1200 Da, and thus their transport through the blood-brain barrier (BBB) is highly restricted. Furthermore, some of the chemotherapeutic drugs also have high plasma binding ratios.

In a preferred embodiment of the present invention, an odorant is presented to an air passage of a patient, such as a nasal cavity or the throat, so as to increase CBF and blood flow to the eye, in order to treat a condition of the eye. Alternatively or additionally, an odorant is similarly presented in order to enhance delivery of therapeutic molecules across the BBB and to the eye, in order to treat a condition of the eye.

Figure 15:
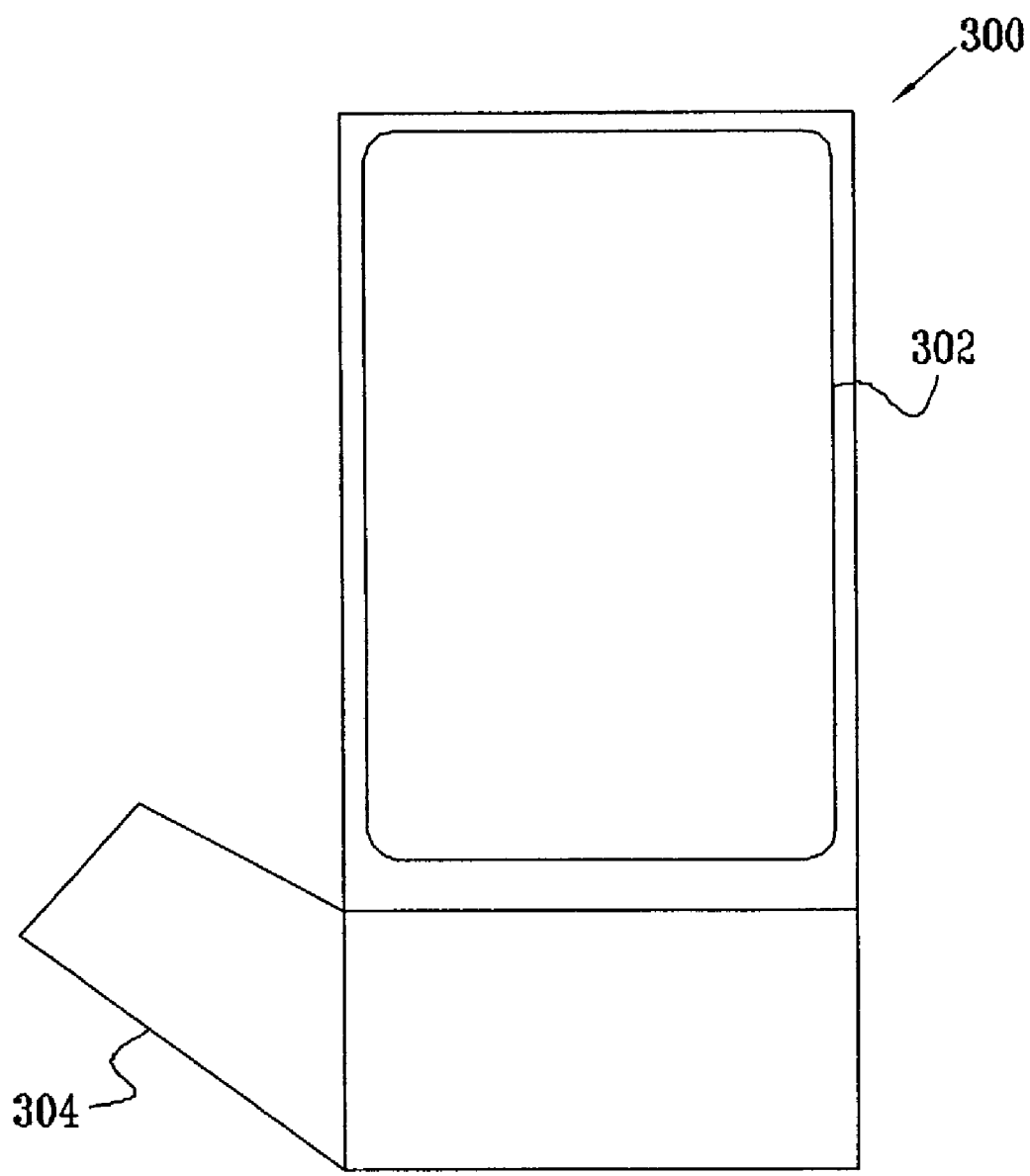
FIG. 15 is a schematic sectional illustration of a nasal inhaler, for use in presenting an odorant to a subject, in accordance with a preferred embodiment of the present invention.

FIG. 15 is a schematic sectional illustration of a nasal inhaler 300, for use in presenting an odorant to a subject, in accordance with a preferred embodiment of the present invention. Nasal inhaler 300 preferably comprises apparatus known in the art, such as an aqueous spray nasal inhaler, a metered dose nasal inhaler, or an air-dilution olfactometer. The odorant is stored in an odorant-storage vessel 302, and is delivered to a nasal passage using an odorant-delivery element 304, such as a nasal piece. Alternatively or additionally, the odorant is presented by means of an orally-dissolvable capsule that releases the active odorants upon contact with salivary liquids. The odorants reach the appropriate neural structures and induce vasodilatation, vasoconstriction and/or cerebrovascular permeability changes.

In a preferred embodiment of the present invention, stimulation of the MTS is achieved by applying a neuroexcitatory agent to the MTS. Suitable neuroexcitatory agents include, but are not limited to acetylcholine and urocholine. For some applications, the MTS is stimulated by applying a neuroinhibitory agent, such as atropine, hexamethonium, or a local anesthetic (e.g., lidocaine).

In a preferred embodiment of the present invention, stimulation of the MTS is achieved by applying mechanical stimulation to the MTS, e.g., vibration.

In a preferred embodiment of the present invention, techniques of electrical, chemical, mechanical and/or odorant stimulation are used to treat a condition of the eye. For some conditions, such as ocular vascular disorders, such stimulation is configured so as to increase cerebral blood flow (CBF), thereby increasing blood flow to various tissues of the eye, so as to treat the condition. Alternatively or additionally, such stimulation is configured to increase permeability of the BBB, in order to enhance delivery of therapeutic molecules across the BBB and into the eye, so as to treat tumors and other conditions of the eye.

In a preferred embodiment of the present invention, conditions of the eye are treated by applying bipolar stimulation, in which a first electrode is applied to a first MTS, and a second electrode is applied to a second MTS. In a preferred example of this technique, a first electrode is applied to the vidian nerve and a second electrode is applied to the SPG.

These stimulation techniques, alone or in combination, are believed to be particularly useful for treating the following eye conditions. It is to be noted that, in the disclosure that follows, any descriptions of possible therapeutic mechanisms are by way of illustration only, and the scope of the present invention includes treatments that result from other mechanisms as well.

Diabetic Retinopathies

Stimulation techniques described herein are used to treat various diabetic retinopathies, including those caused by diabetes mellitus. It is hypothesized that increasing CBF improves blood flow to the eye, thereby improving oxygenation of eye tissue. It is therefore hypothesized that various diabetic retinopathies can be treated by increasing blood flow to the eye, and improving oxygenation of the eye tissue.

Retinal Vein Occlusion

Stimulation techniques described herein are used to treat retinal vein occlusion. It is believed that retinal vein occlusion is caused in part by a build-up of metabolites. It is therefore hypothesized that this condition can be treated by increasing clearance of metabolites from the cells of the eye into the capillaries of the eye. It is further hypothesized that, alternatively or additionally, this condition can be treated by increasing metabolism to the cells of the eyes. The stimulation techniques described herein may achieve one or both of these effects by increasing CBF, increasing blood flow to and in the eyes, and/or increasing BBB permeability, which may also increase the permeability of capillary walls in the eyes. Additionally, increasing blood flow in the eyes typically releases occlusions.

Retinal Artery Occlusion

Stimulation techniques described herein are used to treat retinal artery occlusion, including transient central retinal occlusion. When retinal artery occlusion has occurred, tissue survival can generally be improved by increasing blood flow to the affected tissue (similar to ischemic stroke), and thereby allowing more nutrients to be supplied to the tissue in danger. It is hypothesized that the stimulation techniques described herein increase blood flow to eye tissue by increasing CBF. Alternatively or additionally, the techniques described herein may dilate the vessels leading to the eye, which may allow a blood clot to migrate to a narrower vessel. As a result, the larger vessel is no longer obstructed, and damage is to some extent limited to the lesser amount of tissue supplied by the narrower vessel.

Retinal Detachment

Stimulation techniques described herein are used to treat retinal detachment. It is hypothesized that the stimulation techniques described herein increase CBF, thereby increasing blood flow to the eye, which improves reattachment of the retina.

Tumors of the Eye

Stimulation techniques described herein are used to treat tumors of the eye, such as tumors of the optic nerve and retinal carcinoma, by (a) increasing the permeability of the BBB to large compounds (such as large therapeutic molecules, or small therapeutic molecules bound to large molecules) that would otherwise have lower-than-desired penetration into the tumor and/or (b) increasing CBF, as described hereinabove.

Macular Degeneration

Stimulation techniques described herein are used to treat macular degeneration, including senile macular degeneration. It is hypothesized that increasing CBF increases choroidal blood flow, which arrests and/or decreases the degenerative process associated with macular degeneration. Alternatively or additionally, stimulation techniques described herein are used to treat macular degeneration by increasing the permeability of the BBB to large compounds (such as large therapeutic molecules, or small therapeutic molecules bound to large molecules) that would otherwise have lower-than-desired penetration into the eye.

Glaucoma

Stimulation techniques described herein are used to treat glaucoma, including open- and closed-angle glaucoma. It is hypothesized that increasing CBF increases fluid clearance from the anterior chamber of the eye. Such increased fluid clearance treats the condition by lowering intraocular pressure (IOP), which is elevated in glaucoma.

In a preferred embodiment, the stimulation techniques described herein are used to treat other optic neuropathies, retinal-degeneration diseases, and/or cystoid macular edema (CME).

In a preferred embodiment of the present invention, the electrical, chemical, mechanical and/or odorant stimulation techniques described herein are applied to facilitate a diagnosis of an eye condition of a subject. The increased permeability of the BBB resulting from such stimulation generally causes an increase in molecular passage between the eye and a tissue of the subject, such as blood of the subject. As a result, constituents that can serve as diagnostic indicators, such as proteins, hormones, antibodies, electrolytes, neuropeptides, and enzymes, typically pass from the eye into the systemic blood circulation of the subject, where they can be readily tested to aid in diagnosis of the eye condition. Alternatively, a diagnostic agent is injected into the blood of the subject, and the techniques described herein are used to increase passage of the agent from the blood into at least a portion of tissue of the eye. A diagnostic procedure is then performed on the eye using the diagnostic agent.

In some embodiments of the present invention, techniques described herein are practiced in combination with techniques described in one or more of the above-cited co-assigned provisional patent applications: (i) a U.S. provisional patent application to Lorian et al., filed on even date herewith, entitled, "Surgical tools and techniques for stimulation," (ii) a U.S. provisional patent application to Gross et al., filed on even date herewith, entitled, "Stimulation circuitry and control of electronic medical device," and (iii) a U.S. provisional patent application to Shalev et al., filed on even date herewith, entitled, "Stimulation for treating ear pathologies." All of these applications are incorporated herein by reference.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. For example, elements which are shown in a figure to be housed within one integral unit may, for some applications, be disposed in a plurality of distinct units. Similarly, apparatus for communication and power transmission which are shown to be coupled in a wireless fashion may be, alternatively, coupled in a wired fashion, and apparatus for communication and power transmission which are shown to be coupled in a wired fashion may be, alternatively, coupled in a wireless fashion.

The invention claimed is:

1. A method for treating a condition of an eye of a subject, comprising:

stimulating at least one site of the subject, so as to treat the eye condition, the site selected from the group consisting of: a sphenopalatine ganglion (SPG) of the subject, an anterior ethmoidal nerve of the subject, a posterior ethmoidal nerve of the subject, a communicating branch between an anterior ethmoidal nerve and a retro-orbital branch of an SPG of the subject, a communicating branch between a posterior ethmoidal nerve and a retro-orbital branch of an SPG of the subject, a greater palatine nerve of the subject, a lesser palatine nerve of the subject, a sphenopalatine nerve of the subject, a communicating branch between a maxillary nerve and an SPG of the subject, a nasopalatine nerve of the subject, a posterior nasal nerve of the subject, an infraorbital nerve of the subject, an otic ganglion of the subject, an afferent fiber going into the otic ganglion of the subject, an efferent fiber going out of the otic ganglion of the subject, a vidian nerve of the subject, a greater superficial petrosal nerve of the subject, and a lesser deep petrosal nerve of the subject, wherein stimulating the site comprises comprising the stimulation to cause an increase in a blood flow of the eye, so as to treat the eye condition.

2. A method according to claim 1, wherein the condition includes diabetic retinopathy, and wherein stimulating the site comprises stimulating the site so as to treat the diabetic retinopathy.

3. A method according to claim 1, wherein the condition includes retinal vein occlusion, and wherein stimulating the site comprises stimulating the site so as to treat the retinal vein occlusion.

4. A method according to claim 1, wherein the condition includes retinal artery occlusion, and wherein stimulating the site comprises stimulating the site so as to treat the retinal artery occlusion.

5. A method according to claim 1, wherein the condition includes retinal detachment, and wherein stimulating the site comprises stimulating the site so as to treat the retinal detachment.

6. A method according to claim 1, wherein the condition includes macular degeneration, and wherein stimulating the site comprises stimulating the site so as to treat the macular degeneration.

7. A method according to claim 1, wherein the condition includes glaucoma, and wherein stimulating the site comprises stimulating the site so as to treat the glaucoma.

8. A method according to claim 1, wherein the condition includes an optic neuropathy, and wherein stimulating the site comprises stimulating the site so as to treat the optic neuropathy.

9. A method according to claim 1, wherein the condition includes retinal degeneration, and wherein stimulating the site comprises stimulating the site so as to treat the retinal degeneration.

10. A method according to claim 1, wherein the condition includes cystoid macular edema (CME), and wherein stimulating the site comprises stimulating the site so as to treat the CME.

11. A method according to claim 1, wherein the condition includes a tumor of the eye, and wherein stimulating the site comprises stimulating the site so as to treat the tumor.

12. A method according to claim 11, wherein the condition includes a tumor of an optic nerve of the subject, and wherein stimulating the site comprises stimulating the site so as to treat the tumor of the optic nerve.

13. A method according to claim 11, wherein the condition includes retinal carcinoma, and wherein stimulating the site comprises stimulating the site so as to treat the retinal carcinoma.

14. A method according to claim 1, wherein stimulating the site comprises stimulating the SPG, so as to treat the eye condition.

15. A method according to claim 1, wherein stimulating the site comprises stimulating the anterior ethmoidal nerve, so as to treat the eye condition.

16. A method according to claim 1, wherein stimulating the site comprises stimulating the posterior ethmoidal nerve, so as to treat the eye condition.

17. A method according to claim 1, wherein stimulating the site comprises stimulating a site selected from the group consisting of: the communicating branch between the anterior ethmoidal nerve and the retro-orbital branch of the SPG, and the communicating branch between the posterior ethmoidal nerve and the retro-orbital branch of the SPG, so as to treat the eye condition.

18. A method according to claim 1, wherein stimulating the site comprises stimulating the greater palatine nerve, so as to treat the eye condition.

19. A method according to claim 1, wherein stimulating the site comprises stimulating the lesser palatine nerve, so as to treat the eye condition.

20. A method according to claim 1, wherein stimulating the site comprises stimulating the sphenopalatine nerve, so as to treat the eye condition.

21. A method according to claim 1, wherein stimulating the site comprises stimulating the communicating branch between the maxillary nerve and the SPG, so as to treat the eye condition.

22. A method according to claim 1, wherein stimulating the site comprises stimulating the nasopalatine nerve, so as to treat the eye condition.

23. A method according to claim 1, wherein stimulating the site comprises stimulating the posterior nasal nerve, so as to treat the eye condition.

24. A method according to claim 1, wherein stimulating the site comprises stimulating the infraorbital nerve, so as to treat the eye condition.

25. A method according to claim 1, wherein stimulating the site comprises stimulating the otic ganglion, so as to treat the eye condition.

26. A method according to claim 1, wherein stimulating the site comprises stimulating the afferent fiber going into the otic ganglion of the subject, so as to treat the eye condition.

27. A method according to claim 1, wherein stimulating the site comprises stimulating the efferent fiber going out of the otic ganglion of the subject, so as to treat the eye condition.

28. A method according to claim 1, wherein stimulating the site comprises stimulating the vidian nerve, so as to treat the eye condition.

29. A method according to claim 28, wherein stimulating the vidian nerve comprises stimulating the greater superficial petrosal nerve of the subject, so as to treat the eye condition.

30. A method according to claim 28, wherein stimulating the vidian nerve comprises stimulating the lesser deep petrosal nerve of the subject, so as to treat the eye condition.

31. A method according to claim 1, wherein stimulating the site comprises configuring the stimulation to cause an increase in cerebral blood flow (CBF) of the subject, so as to treat the eye condition.

32. A method according to claim 1, wherein stimulating the site comprises configuring the stimulation to cause an increase in molecular passage across a blood brain barrier (BBB) of the subject.

33. A method according to claim 32, wherein configuring the stimulation comprises configuring the stimulation such that the increased molecular passage across the BBB is of a magnitude that increases passage of a therapeutic agent from a systemic blood circulation of the patient through the BBB into a vicinity of the eye of the subject, so as to treat the eye condition.

34. A method according to claim 1, wherein stimulating the site comprises driving a current into the site.

35. A method according to claim 34, wherein driving the current comprises driving the current at a stimulation site in or adjacent to an orbital cavity of the subject.

36. A method according to claim 34, wherein driving the current comprises driving the current into an ethmoidal nerve of the subject.

37. A method according to claim 36, wherein driving the current comprises driving the current into an anterior ethmoidal nerve of the subject.

38. A method according to claim 36, wherein driving the current comprises driving the current into a posterior ethmoidal nerve of the subject.

39. A method according to claim 34, wherein the site includes a first site and a second site, different from the first site, and wherein driving the current comprises driving the current between the first site and the second site.

40. A method according to claim 39,
wherein the first site includes the vidian nerve of the subject, and the second site includes the SPG of the subject, and
wherein driving the current comprises driving the current between the vidian nerve and the SPG.

41. A method according to claim 1, wherein stimulating the site comprises applying a neuroexcitatory agent to the site, so as to stimulate the site.

42. A method according to claim 41, wherein applying the neuroexcitatory agent comprises applying acetylcholine to the site, so as to stimulate the site.

43. A method according to claim 41, wherein applying the neuroexcitatory agent comprises applying urocholine to the site, so as to stimulate the site.

44. A method according to claim 1, wherein stimulating the site comprises applying mechanical stimulation to the site, so as to stimulate the site.

45. A method according to claim 44, wherein applying the mechanical stimulation comprises applying vibration to the site, so as to stimulate the site.

46. A method according to claim 1, wherein configuring the stimulation comprises configuring the stimulation such that the increased blood flow is of a magnitude that increases clearance of a substance from at least a portion of the eye, so as to treat the eye condition.

47. A method according to claim 46, wherein the substance includes a fluid contained in an anterior chamber of the eye, and wherein configuring the stimulation comprises configuring the stimulation to cause increased clearance of the fluid from the anterior chamber so as to lower an intraocular pressure of the eye, so as to treat the eye condition.

48. A method according to claim 1, wherein stimulating the at least one site comprises configuring the stimulation to induce parasympathetic activation of the at least one site.

49. A method according to claim 1, wherein stimulating the at least one site comprises configuring the stimulation to block parasympathetic neural activity of the at least one site.

* * * * *